United States Patent

Kobayashi et al.

Patent Number: 5,942,615
Date of Patent: Aug. 24, 1999

[54] PHENOTHIAZINE OR PHENOXAZINE DERIVATIVE, CHARGE-TRANSPORTING MATERIAL COMPRISING THE SAME, AND ELECTROPHOTOGRAPHIC PHOTORECEPTOR

[75] Inventors: Tohru Kobayashi; Yoshimasa Matsushima; Hiroshi Sugiyama; Toshimitsu Hagiwara, all of Kanagawa, Japan

[73] Assignee: Takasago International Corporation, Tokyo, Japan

[21] Appl. No.: 08/909,937

[22] Filed: Aug. 12, 1997

[30] Foreign Application Priority Data

Aug. 14, 1996 [JP] Japan ................................. 8-231295

[51] Int. Cl.$^6$ ............... C07D 279/22; C07D 279/24; C07D 265/38; G03G 5/06
[52] U.S. Cl. ................. 544/38; 430/59; 544/41; 544/102
[58] Field of Search .............. 544/38, 41, 102

[56] References Cited

U.S. PATENT DOCUMENTS

| | | | |
|---|---|---|---|
| 3,791,826 | 2/1974 | Cherry et al. | 196/1.5 |
| 5,183,718 | 2/1993 | Ueda | 430/59 |
| 5,246,808 | 9/1993 | Hanantani et al. | 430/59 |

FOREIGN PATENT DOCUMENTS

| | | |
|---|---|---|
| 3333557 | 3/1984 | Germany . |
| 60-175052 | 9/1985 | Japan . |
| 62-120346 | 6/1987 | Japan . |
| 01-217357 | 8/1989 | Japan . |
| 06271846 | 9/1994 | Japan . |

OTHER PUBLICATIONS

Asahi Glass, Chemical Abstracts 100: 35831g, Aug. 1983.

*Primary Examiner*—Mark L Berch
*Attorney, Agent, or Firm*—Sughrue, Mion, Zinn, Macpeak & Seas, PLLC

[57] ABSTRACT

A phenothiazine or phenoxazine derivative represented by the following general formula (1), a charge-transporting material comprising the derivative, and an electrophotographic photoreceptor containing the charge-transporting material are disclosed. The charge-transporting material has good solubility in binder polymers, satisfactory sensitivity, and a low residual potential

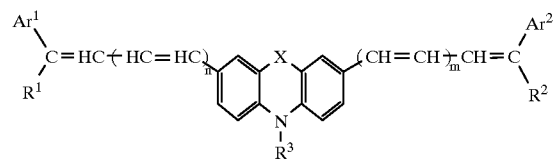

(1)

In general formula (1) $Ar^1$ and $Ar^2$ may be the same or different and each represents an optionally substituted aryl group; $R^1$ and $R^2$ may be the same or different and each represents a hydrogen atom, a lower alkyl group, or an optionally substituted aryl group; $R^3$ represents a lower alkyl group, an alicyclic hydrocarbon group having 5 to 7 carbon atoms, an optionally substituted aryl group, or an optionally substituted aralkyl group; X represents a sulfur atom or an oxygen atom; and n and m each represents an integer of 0 or 1.

1 Claim, No Drawings

PHENOTHIAZINE OR PHENOXAZINE DERIVATIVE, CHARGE-TRANSPORTING MATERIAL COMPRISING THE SAME, AND ELECTROPHOTOGRAPHIC PHOTORECEPTOR

FIELD OF THE INVENTION

The present invention relates to a phenothiazine or phenoxazine derivative represented by the following general formula (1):

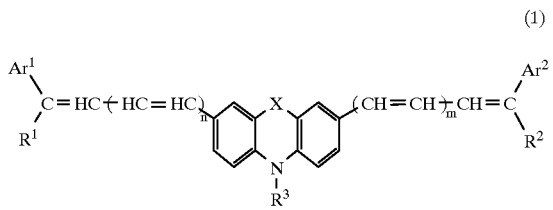

wherein $Ar^1$ and $Ar^2$ may be the same or different and each represents an optionally substituted aryl group; $R^1$ and $R^2$ may be the same or different and each represents a hydrogen atom, a lower alkyl group, or an optionally substituted aryl group; $R^3$ represents a lower alkyl group, an alicyclic hydrocarbon group having 5 to 7 carbon atoms, an optionally substituted aryl group, or an optionally substituted aralkyl group; X represents a sulfur atom or an oxygen atom; and n and m each represents an integer of 0 or 1. This invention further relates to a charge-transporting material comprising the phenothiazine or phenoxazine derivative and to an electrophotographic photoreceptor containing the charge-transporting material.

BACKGROUND OF THE INVENTION

Inorganic photoconductive materials recently in use include amorphous silicon, amorphous selenium, cadmium sulfide, zinc oxide, and the like. However, some of these materials are expensive because of difficulties in production thereof, while others are toxic and disadvantageous from the standpoint of environmental protection.

On the other hand, as organic photoconductors, ones of the type comprising, in particular, a charge-generating material and a charge-transporting material which respectively perform their functions are proposed extensively (see, e.g., U.S. Pat. No. 3,791,826). In this type, there is the possibility that a high-sensitivity electrophotographic photoreceptor might be obtained by using a substance which efficiently generates carriers (The term "carriers" means "charges"; the same applies hereinafter.) as the charge-generating material in combination with a substance having high charge-transporting ability as the charge-transporting material.

Of these materials, the charge-transporting material is required to efficiently receive the carriers generated in the charge-generating material upon light irradiation in an electric field and permit them to rapidly move through the photosensitive layer to extinguish the surface charges promptly. The speed at which carriers move per unit electric field is called carrier mobility. A high carrier mobility means that carriers rapidly move in the charge-transporting layer. Any charge-transporting substance has its intrinsic carrier mobility and, hence, it is necessary that for attaining a high carrier mobility, a material having a high carrier mobility be employed. However, the attainable carrier mobilities have not yet reached a sufficient level.

In the case of applying a solution of a charge-transporting substance and a binder polymer in an organic solvent, it is necessary to form a thin homogeneous organic coating film free from crystallization and pinhole formation. This is because when a high electric field is applied to the thin film obtained, the part having microcrystals or pinholes undergoes dielectric breakdown or causes noise.

In addition to the satisfactory properties of the charge-generating substance and of the charge-transporting substance, it is also important that carriers should be efficiently injected from the charge-generating substance into the charge-transporting substance, i.e., from the charge-generating layer into the charge-transporting layer. This injection of charges depends on the properties of the interface between the charge-generating substance (or charge-generating layer) and the charge-transporting substance (or charge-transporting layer) and varies with combinations of various substances. Since a charge-transporting material should meet various requirements as described above, charge-transporting substances having a variety of properties are being developed.

Among conventional charge-transporting materials, a styryl compound represented by the following general formula (A) has, for example, been proposed in JP-A-60-175052 (the term "JP-A" as used herein means an "unexamined published Japanese patent application"):

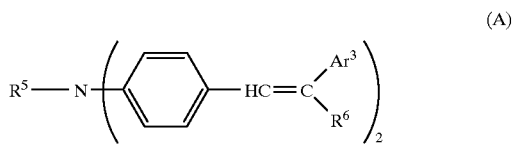

wherein $R^5$ represents an optionally substituted alkyl group or an optionally substituted aryl group, $R^6$ represents a hydrogen atom, an optionally substituted alkyl group, or an optionally substituted aryl group, and $Ar^3$ represents an optionally substituted aryl group. Furthermore, compounds similar to compound (A) described above have been proposed, for example, in JP-A-62-120346, JP-A-1-217357, JP-A-4-57056, and JP-A-4-292663.

In JP-A-6-271846 is disclosed the use of part of the compounds of the present invention as an organic electroluminescent element. The following compound (B) is shown in an Example given therein.

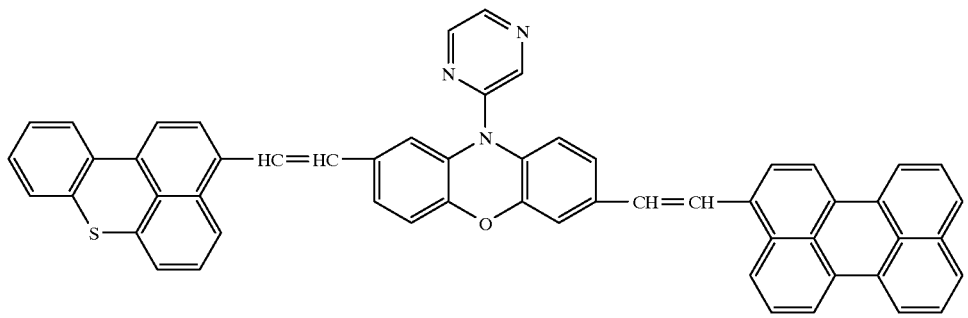

(B)

However, the compounds described in JP-A-6-271846 are not known at all as materials useful in electrophotographic photoreceptors, not to mention as charge-transporting materials.

Furthermore, there is a description in JP-A-4-57056 to the effect that the following compound (C) partly separated out as crystals during the preparation of a photoreceptor because of the poor solubility of the compound in binder polymers.

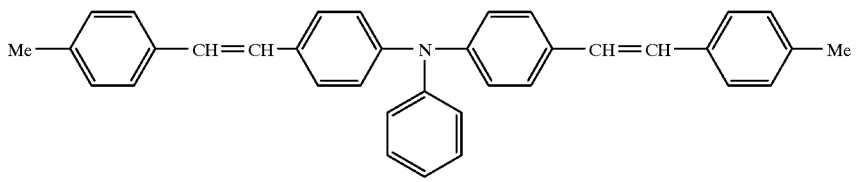

(C)

With the recent increasing demand for charge-transporting materials, a new material capable of coping with various conditions is desired.

Specifically, there is a desire for a new charge-transporting material which is satisfactory in solubility in binder polymers and other properties and is capable of exhibiting satisfactory electrophotographic properties including high sensitivity.

SUMMARY OF THE INVENTION

An object of the present invention is to provide a novel charge-transporting material which has good solubility and gives an electrophotographic photoreceptor having excellent properties including a low residual potential and high sensitivity.

As a result of intensive studies made by the present inventors on a wide range of compounds under these circumstances, they have found that the problems described above can be eliminated with a 10-substituted phenothiazine or phenoxazine derivative which has an arylvinyl- or arylbutadienyl-framework substituent in each of the 3- and 7-positions and is represented by the following general formula (1):

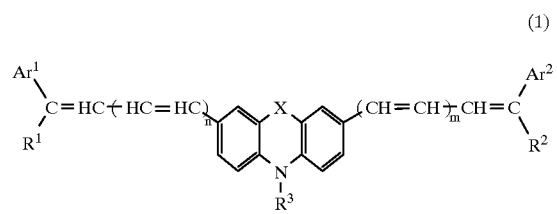

(1)

wherein $Ar^1$ and $Ar^2$ may be the same or different and each represents an optionally substituted aryl group; $R^1$ and $R^2$ may be the same or different and each represents a hydrogen atom, a lower alkyl group, or an optionally substituted aryl group; $R^3$ represents a lower alkyl group, an alicyclic hydrocarbon group having 5 to 7 carbon atoms, an optionally substituted aryl group, or an optionally substituted aralkyl group; X represents a sulfur atom or an oxygen atom; and n and m each represents an integer of 0 or 1. The present invention has been completed based on this finding.

That is, the present inventors have found that compound (1) has good solubility in binder polymers and other ingredients and suffers neither crystallization nor pinhole formation, and that a photoreceptor employing this compound has high sensitivity and a low residual potential.

Accordingly, the first aspect of the present invention relates to a phenothiazine or phenoxazine derivative represented by the following general formula (1):

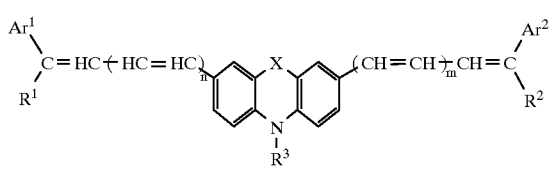

(1)

wherein Ar¹, Ar², R¹, R², R³, X, n and m have the same meanings as defined above.

The second aspect of the present invention relates to a phenothiazine or phenoxazine derivative represented by the above general formula (1) wherein the substituent groups of Ar¹, Ar², R¹, R² and R³ are further restricted, and either of n and m is 1 and the other is 0, or wherein n and m each is 1.

The third aspect of the present invention relates to a charge-transporting material comprising the phenothiazine or phenoxazine derivative represented by general formula (1) according to the first or second aspect of the present invention.

The fourth aspect of the present invention relates to an electrophotographic photoreceptor containing the charge-transporting material according to the third aspect of the present invention.

DETAILED DESCRIPTION OF THE INVENTION

In compound (1) of the present invention, Ar¹ and Ar² may be the same or different. Examples thereof include unsubstituted aryl groups such as phenyl and naphthyl, lower-alkyl-substituted phenyl groups such as o-tolyl, m-tolyl, p-tolyl, and xylyl, lower alkoxy-substituted phenyl groups such as methoxyphenyl, ethoxyphenyl, and propoxyphenyl, halogen-substituted phenyl groups such as chlorophenyl, bromophenyl, fluorophenyl, and iodophenyl, and amino-substituted phenyl groups such as diarylaminos and dialkylaminos. R¹ and R² may be the same or different, and each represents a hydrogen atom, a lower alkyl group, or an optionally substituted aryl group. Examples of the lower alkyl group include alkyl groups having 1 to 4 carbon atoms, such as methyl, ethyl, n-propyl, isopropyl, n-butyl, s-butyl, and t-butyl. Examples of the optionally substituted aryl group include the same unsubstituted and substituted aryl groups as those enumerated above with regard to Ar¹ and Ar².

Examples of R³ include the same lower alkyl groups as those enumerated above with regard to R¹ and R², the same unsubstituted and substituted aryl groups as those enumerated above with regard to Ar¹ and Ar², alicyclic hydrocarbon groups having 5 to 7 carbon atoms, such as cyclopentyl, cyclohexyl, and cycloheptyl, and optionally substituted aralkyl groups such as benzyl, tolylmethyl, methoxybenzyl, and chlorobenzyl.

Specific preferred examples of the compound of the present invention represented by general formula (1) are given in the following Tables 1 to 4. However, the compound of the present invention should not be construed as being limited to these examples.

The abbreviations used for substituents in the Tables have the following meanings.

Me: methyl
Et: ethyl
Pr: propyl
Bu: butyl
Ph: phenyl
Naph: naphthyl
MeO: methoxy Some substituent abbreviations contain one or more numerals which each indicates the position of substitution. For example, Ph-(2)Me(4)Me means a phenyl group having methyl groups respectively in the 2- and 4-positions, and 1-Naph means a naphthyl group bonded in the 1-position.

TABLE 1

| Exemplified Compound | n | m | X | Ar¹ | R¹ | Ar² | R² | R³ |
|---|---|---|---|---|---|---|---|---|
| 1 | 0 | 0 | S | Ph | Ph | Ph | Ph | Me |
| 2 | 1 | 1 | S | Ph | Ph | Ph | Ph | Me |
| 3 | 0 | 0 | S | Ph | Me | Ph | Me | Me |
| 4 | 0 | 0 | S | Ph | Ph | Ph | Ph | Et |
| 5 | 0 | 0 | S | Ph | Ph | Ph—(3)Me | Ph—(3)Me | Et |
| 6 | 0 | 1 | S | Ph | Ph | Ph | Ph | Et |
| 7 | 0 | 0 | S | Ph | Ph | Ph | 2-Naph | Et |
| 8 | 0 | 0 | S | Ph—(2)Me(4)Me | Ph—(2)Me(4)Me | Ph—(2)Me(4)Me | Ph—(2)Me(4)Me | Et |
| 9 | 0 | 0 | S | Ph—(4)Cl | Ph | Ph—(4)Cl | Ph | Et |
| 10 | 1 | 1 | S | 1-Naph | Ph | 1-Naph | Ph | Et |
| 11 | 1 | 1 | S | Ph—(4)MeO | Ph | Ph—(4)MeO | Ph | Et |
| 12 | 1 | 1 | S | Ph | Ph | Ph | Ph | Et |
| 13 | 0 | 0 | S | Ph | Me | Ph | Me | Et |
| 14 | 0 | 0 | S | Ph | Ph | Ph | Ph | iPr |
| 15 | 1 | 1 | S | Ph | Ph | Ph | Ph | iPr |
| 16 | 1 | 1 | S | Ph—(4)Me | Ph | Ph—(4)Me | Ph | iPr |
| 17 | 0 | 0 | S | Ph—(3)Me | Ph—(3)Me | Ph—(3)Me | Ph—(3)Me | iPr |
| 18 | 1 | 1 | S | Ph—(3)Me | Ph | Ph—(3)Me | Ph | iPr |
| 19 | 0 | 0 | S | Ph | Ph | Ph | Ph | Ph |
| 20 | 0 | 1 | S | Ph | Ph | Ph | Ph | Ph |
| 21 | 1 | 1 | S | Ph | Ph | Ph | Ph | Ph |
| 22 | 0 | 0 | S | Ph | Ph | Ph | Ph | Ph—(4)Me |
| 23 | 1 | 1 | S | Ph | Ph | Ph | Ph | Ph—(4)Me |
| 24 | 0 | 0 | S | Ph | Ph—(3)Me | Ph | Ph—(3)Me | CH₂Ph |
| 25 | 1 | 1 | S | Ph—(4)Me | Ph—(4)Me | Ph—(4)Me | Ph—(4)Me | CH₂Ph |
| 26 | 0 | 0 | S | Ph | Ph | Ph | Ph | s-Bu |
| 27 | 1 | 1 | S | Ph | Ph | Ph | Ph | s-Bu |

TABLE 2

| Exemplified Compound | n | m | X | Ar¹ | R¹ | Ar² | R² | R³ |
|---|---|---|---|---|---|---|---|---|
| 28 | 0 | 0 | S | Ph | H | Ph | H | n-Bu |
| 29 | 1 | 1 | S | Ph | Ph | Ph | Ph | n-Bu |
| 30 | 0 | 0 | S | Ph | Me | Ph | Me | n-Bu |
| 31 | 0 | 0 | S | Ph | Ph | Ph | Ph | n-Pr |
| 32 | 0 | 0 | S | Ph | Ph | Ph—(3)Me | Ph—(3)Me | n-Pr |
| 33 | 0 | 1 | S | Ph | Ph | Ph | Ph | n-Pr |
| 34 | 0 | 0 | S | Ph | Ph | Ph | 2-Naph | n-Pr |
| 35 | 0 | 0 | S | Ph—(2)Me(4)Me | Ph—(2)Me(4)Me | Ph—(2)Me(4)Me | Ph—(2)Me(4)Me | n-Pr |
| 36 | 0 | 0 | S | Ph—(4)Cl | Ph | Ph—(4)Cl | Ph | n-Pr |
| 37 | 1 | 1 | S | 1-Naph | Ph | 1-Naph | Ph | n-Pr |
| 38 | 1 | 1 | S | Ph—(4)MeO | Ph | Ph—(4)MeO | Ph | n-Pr |
| 39 | 1 | 1 | S | Ph | H | Ph | H | n-Pr |
| 40 | 0 | 0 | S | Ph | Me | Ph | Me | t-Bu |
| 41 | 0 | 0 | S | Ph | Ph | Ph | Ph | t-Bu |
| 42 | 1 | 1 | S | Ph | Ph | Ph | Ph | t-Bu |
| 43 | 1 | 1 | S | Ph—(4)Me | Ph | Ph—(4)Me | Ph | t-Bu |
| 44 | 0 | 0 | S | Ph—(3)Me | Ph—(3)Me | Ph—(3)Me | Ph—(3)Me | t-Bu |
| 45 | 1 | 1 | S | Ph—(3)Me | Ph | Ph—(3)Me | Ph | t-Bu |
| 46 | 0 | 0 | S | Ph | Ph | Ph | Ph | Ph—(4)Br |
| 47 | 0 | 1 | S | Ph | Ph | Ph | Ph | Ph—(4)Br |
| 48 | 1 | 1 | S | Ph | Ph | Ph | Ph | Ph—(4)Br |
| 49 | 0 | 0 | S | Ph | Ph | Ph | Ph | Ph—(3)Me |
| 50 | 1 | 1 | S | Ph | Ph | Ph | Ph | Ph—(3)Me |
| 51 | 0 | 0 | S | Ph | Ph—(3)Me | Ph | Ph—(3)Me | Ph—(4)MeO |
| 52 | 1 | 1 | S | Ph—(4)Me | Ph—(4)Me | Ph—(4)Me | Ph—(4)Me | Ph—(4)MeO |
| 53 | 0 | 0 | S | Ph | Ph | Ph | Ph | cyclohexyl |
| 54 | 1 | 1 | S | Ph | Ph | Ph | Ph | cyclohexyl |

TABLE 3

| Exemplified Compound | n | m | X | Ar¹ | R¹ | Ar² | R² | R³ |
|---|---|---|---|---|---|---|---|---|
| 55 | 0 | 0 | O | Ph | Ph | Ph | Ph | Me |
| 56 | 1 | 1 | O | Ph | Ph | Ph | Ph | Me |
| 57 | 0 | 0 | O | Ph | Me | Ph | Me | Me |
| 58 | 0 | 0 | O | Ph | Ph | Ph | Ph | Et |
| 59 | 0 | 0 | O | Ph | Ph | Ph—(3)Me | Ph—(3)Me | Et |
| 60 | 0 | 1 | O | Ph | Ph | Ph | Ph | Et |
| 61 | 0 | 0 | O | Ph | Ph | Ph | 2-Naph | Et |
| 62 | 0 | 0 | O | Ph—(2)Me(4)Me | Ph—(2)Me(4)Me | Ph—(2)Me(4)Me | Ph—(2)Me(4)Me | Et |
| 63 | 0 | 0 | O | Ph—(4)Cl | Ph | Ph—(4)Cl | Ph | Et |
| 64 | 1 | 1 | O | 1-Naph | Ph | 1-Naph | Ph | Et |
| 65 | 1 | 1 | O | Ph—(4)MeO | Ph | Ph—(4)MeO | Ph | Et |
| 66 | 1 | 1 | O | Ph | Ph | Ph | Ph | Et |
| 67 | 0 | 0 | O | Ph | Me | Ph | Me | iPr |
| 68 | 0 | 0 | O | Ph | Ph | Ph | Ph | iPr |
| 69 | 1 | 1 | O | Ph | Ph | Ph | Ph | iPr |
| 70 | 1 | 1 | O | Ph—(4)Me | Ph | Ph—(4)Me | Ph | iPr |
| 71 | 0 | 0 | O | Ph—(3)Me | Ph—(3)Me | Ph—(3)Me | Ph—(3)Me | iPr |
| 72 | 1 | 1 | O | Ph—(3)Me | Ph | Ph—(3)Me | Ph | iPr |
| 73 | 0 | 0 | O | Ph | Ph | Ph | Ph | Ph |
| 74 | 0 | 1 | O | Ph | Ph | Ph | Ph | Ph |
| 75 | 1 | 1 | O | Ph | Ph | Ph | Ph | Ph |
| 76 | 0 | 0 | O | Ph | H | Ph | H | Ph—(4)Me |
| 77 | 1 | 1 | O | Ph | H | Ph | H | Ph—(4)Me |
| 78 | 0 | 0 | O | Ph | Ph—(3)Me | Ph | Ph—(3)Me | CH₂Ph |
| 79 | 1 | 1 | O | Ph—(4)Me | Ph—(4)Me | Ph—(4)Me | Ph—(4)Me | CH₂Ph |
| 80 | 0 | 0 | O | Ph | Ph | Ph | Ph | s-Bu |
| 81 | 1 | 1 | O | Ph | Ph | Ph | Ph | s-Bu |

TABLE 4

| Exemplified Compound | n | m | X | Ar¹ | R¹ | Ar² | R² | R³ |
|---|---|---|---|---|---|---|---|---|
| 82 | 0 | 0 | O | Ph | Ph | Ph | Ph | n-Bu |
| 83 | 1 | 1 | O | Ph | Ph | Ph | Ph | n-Bu |
| 84 | 0 | 0 | O | Ph | Me | Ph | Me | n-Bu |
| 85 | 0 | 0 | O | Ph | Ph | Ph | Ph | n-Pr |
| 86 | 0 | 0 | O | Ph | Ph | Ph—(3)Me | Ph—(3)Me | n-Pr |

TABLE 4-continued

| Exemplified Compound | n | m | X | Ar¹ | R¹ | Ar² | R² | R³ |
|---|---|---|---|---|---|---|---|---|
| 87 | 0 | 1 | 0 | Ph | Ph | Ph | Ph | n-Pr |
| 88 | 0 | 0 | 0 | Ph | Ph | Ph | 2-Naph | n-Pr |
| 89 | 0 | 0 | 0 | Ph—(2)Me(4)Me | Ph—(2)Me(4)Me | Ph—(2)Me(4)Me | Ph—(2)Me(4)Me | n-Pr |
| 90 | 0 | 0 | 0 | Ph—(4)Cl | Ph | Ph—(4)Cl | Ph | n-Pr |
| 91 | 1 | 1 | 0 | 1-Naph | Ph | 1-Naph | Ph | n-Pr |
| 92 | 1 | 1 | 0 | Ph—(4)MeO | Ph | Ph—(4)MeO | Ph | n-Pr |
| 93 | 1 | 1 | 0 | Ph | Ph | Ph | Ph | n-Pr |
| 94 | 0 | 0 | 0 | Ph | Me | Ph | Me | t-Bu |
| 95 | 0 | 0 | 0 | Ph | Ph | Ph | Ph | t-Bu |
| 96 | 1 | 1 | 0 | Ph | Ph | Ph | Ph | t-Bu |
| 97 | 1 | 1 | 0 | Ph—(4)Me | Ph | Ph—(4)Me | Ph | t-Bu |
| 98 | 0 | 0 | 0 | Ph—(3)Me | Ph—(3)Me | Ph—(3)Me | Ph—(3)Me | t-Bu |
| 99 | 1 | 1 | 0 | Ph—(3)Me | Ph | Ph—(3)Me | Ph | t-Bu |
| 100 | 0 | 0 | 0 | Ph | Ph | Ph | Ph | Ph—(4)Br |
| 101 | 0 | 1 | 0 | Ph | Ph | Ph | Ph | Ph—(4)Br |
| 102 | 1 | 1 | 0 | Ph | Ph | Ph | Ph | Ph—(4)Br |
| 103 | 0 | 0 | 0 | Ph | Ph | Ph | Ph | Ph—(3)Me |
| 104 | 1 | 1 | 0 | Ph | Ph | Ph | Ph | Ph—(3)Me |
| 105 | 0 | 0 | 0 | Ph | Ph—(3)Me | Ph | Ph—(3)Me | Ph—(4)MeO |
| 106 | 1 | 1 | 0 | Ph—(4)Me | Ph—(4)Me | Ph—(4)Me | Ph—(4)Me | Ph—(4)MeO |
| 107 | 0 | 0 | 0 | Ph | Ph | Ph | Ph | cyclohexyl |
| 108 | 1 | 1 | 0 | Ph | Ph | Ph | Ph | cyclohexyl |

The 3,7-bisvinylphenothiazines and 3,7-bisvinylphenoxazines (1a) represented by general formula (1) wherein n=m=0, Ar¹=Ar², and R¹=R² can be synthesized according to reaction scheme 1:

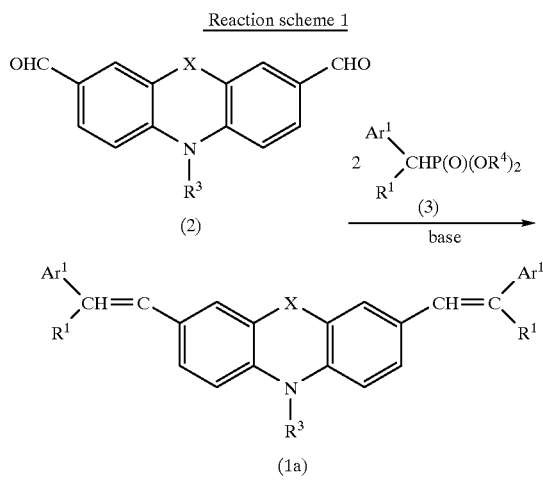

Reaction scheme 1 wherein Ar¹, R¹, R³, and X have the same meanings as defined above, and R⁴ represents a lower alkyl group.

R⁴ represents methyl, ethyl, propyl, or butyl, especially desirably methyl or ethyl.

Specifically, a 10-substituted 3,7-diformylphenothiazine or 10-substituted 3,7-diformylphenoxazine (2) is reacted with 2 mol of an alkylphosphonic ester (3) per mol of compound (2) in the presence of a base at a temperature of from room temperature to about 80° C., whereby the target compound can be easily produced. Examples of the base include sodium hydroxide, potassium hydroxide, sodium amide, sodium hydride, and metal alkoxides such as sodium methoxide, sodium tert-butoxide, and potassium tert-butoxide. The amount of the base is at least 1 time, preferably from 1.1 to 1.5 times, that of the alkylphosphonic ester (3). A solvent can be used such as a lower alcohol, e.g., methanol or ethanol, an ether, e.g., 1,2-dimethoxyethane, diethyl ether, tetrahydrofuran, or dioxane, a hydrocarbon, e.g., toluene or xylene, or an aprotic polar solvent, e.g., dimethyl sulfoxide, N,N-dimethylformamide, N,N-dimethylacetamide, or N-methylpyrrolidone, or a mixture of two or more of these. A suitable reaction temperature can be selected from a wide range according to factors such as the solvent and base used and the reactivity of the substrate. For example, the reaction is conducted at 0° to 150° C., preferably from room temperature to 80° C.

The 10-substituted 3,7-diformylphenothiazine or 10-substituted 3,7-diformylphenoxazine (2) can be obtained by subjecting a 10-substituted phenothiazine or 10-substituted phenoxazine (4) to the Vilsmeier-Haak reaction in the presence of a Lewis acid or a protonic acid (reaction scheme 2). The amount of the Lewis or protonic acid is preferably from 1 to 2 times that of the 10-substituted 3,7-diformylphenothiazine or 10-substituted 3,7-diformylphenoxazine (2):

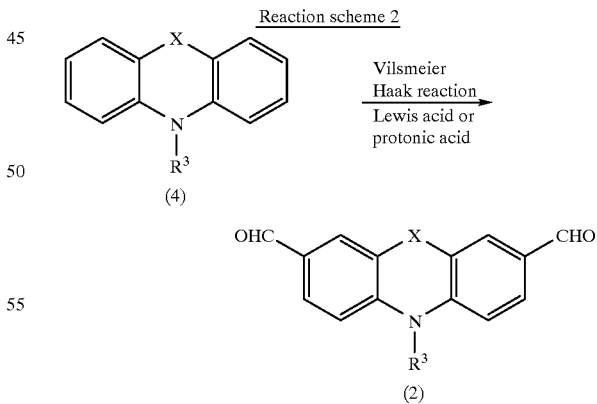

Reaction scheme 2 wherein R³ and X have the same meanings as define above.

The alkylphosphonic ester (3) is obtained by heating a mixture of the corresponding aralkyl chloride or bromide and a trialkyl phosphite either directly or in a solvent such as toluene or xylene.

On the other hand, the 3,7-bisvinylphenothiazines and 3,7-bisvinylphenoxazines (1b) represented by general formula (1) wherein n=m=0, $Ar^1$ and $Ar^2$ may be the same or different, and $R^1$ and $R^2$ may be the same or different can be synthesized according to reaction scheme 3:

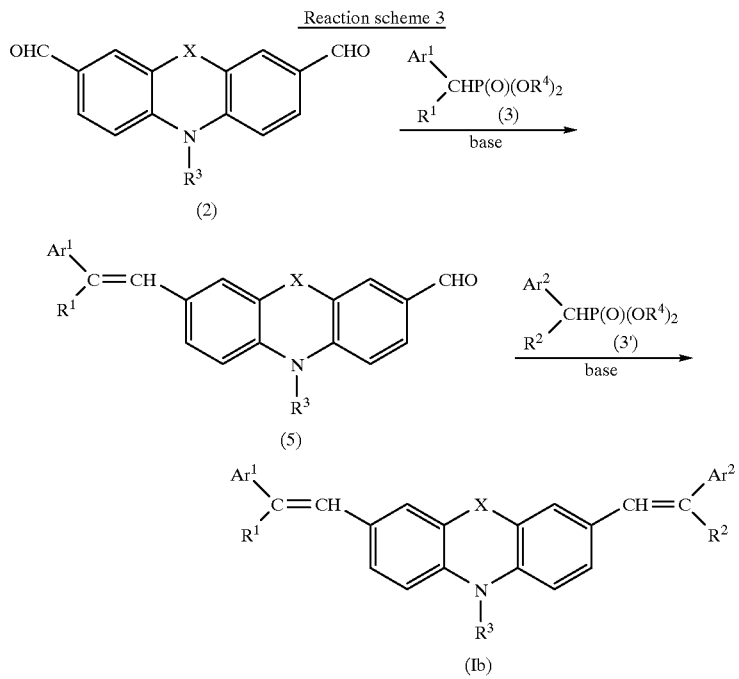

wherein $Ar^1$, $R^1$, $Ar^2$, $R^2$, $R^3{}_1$ and X have the same meanings as defined above, and $R^4$ represents a lower alkyl group.

Specifically, a 10-substituted 3,7-diformylphenothiazine or 10-substituted 3,7-diformylphenoxazine (2) is reacted with an equimolar amount of an alkylphosphonic ester (3) in the presence of a base to synthesize a 10-substituted 3-vinyl-7-formylphenothiazine or 10-substituted 3-vinyl-7-formylphenoxazine (5). Compound (5) is reacted with an alkylphosphonic ester, which is different from the alkylphosphonic ester (3) used above, to synthesize the target compound (1b) according to the present invention.

In the case where $R^1$ and $R^2$ each is not a hydrogen atom, compound (5) can be obtained also by subjecting a 10-substituted 3-vinylphenothiazine or 10-substituted 3-vinylphenoxazine (6) to the ordinary Vilsmeier-Haak reaction (reaction scheme 4):

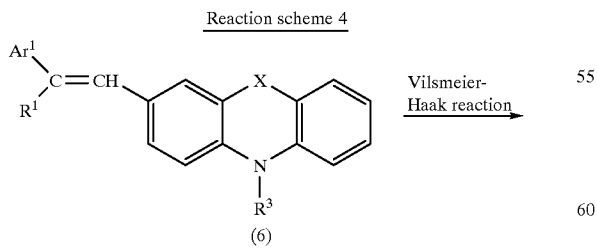

-continued

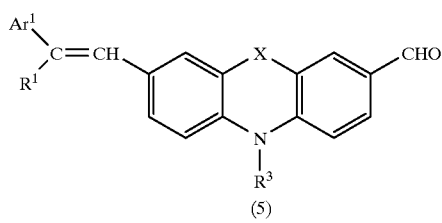

wherein $Ar^1$, $R^1$, $R^3$, and X have the same meanings as defined above.

On the other hand, the phenothiazine derivatives and phenoxazine derivatives (1c) represented by general formula (1) wherein n=0 and m=1 can be synthesized according to reaction scheme 5:

Reaction scheme 5

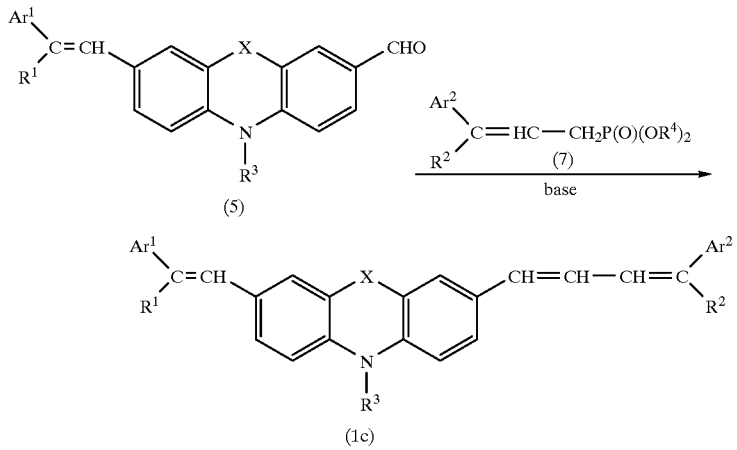

wherein $Ar^1$, $R^1$, $Ar^2$, $R^2$, and $R^3$ have the same meanings as defined above, and $R^4$ represents a lower alkyl group.

Specifically, the monoformyl compound (5) synthesized above according to reaction scheme 3 or 4 is reacted with a 3-arylallylphosphonic acid dialkyl ester (7), whereby the target compound can be obtained.

The 3-arylallylphosphonic acid dialkyl ester (7) can be obtained according to reaction scheme 6:

acid according to the method described in JP-A-49-75564 to obtain a 3-arylallyl chloride (11). A mixture of this 3-arylallyl chloride (11) and a trialkyl phosphite is heated either directly or in a solvent such as toluene or xylene, whereby the 3-arylallylphosphonic acid dialkyl ester (7) can be obtained.

Examples of the alkyl groups of the trialkyl phosphite include lower alkyl groups such as methyl, ethyl, propyl, and butyl. Of these, methyl and ethyl are especially preferred.

Reaction scheme 6

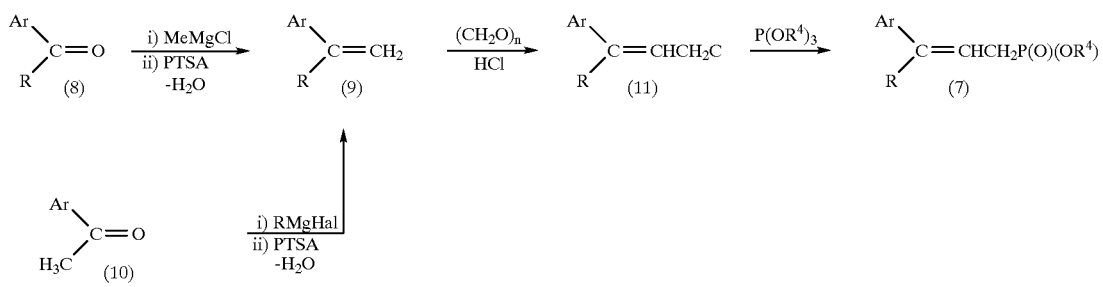

wherein Ar represents $Ar^1$ or $Ar^2$, which each is as defined above; R represents $R^1$ or $R^2$, which each is as defined above; Hal represents a halogen atom; and $R^4$ represents a lower alkyl group.

Specifically, an arylethylene (9) is first obtained by (i) reacting a carbonyl derivative (8) with methylmagnesium chloride (MeMgCl) and then (ii) dehydrating the resultant alcohol in the presence of an acid. Usable as the acid is one ordinarily used for dehydration reaction, such as, e.g., p-toluenesulfonic acid (PTSA).

The arylethylene (9) can be obtained also by conducting the same reactions (i) and (ii) described above, except that a ketone derivative (10) is used as a starting compound and that an R-MgHal is used in place of methylmagnesium chloride.

Subsequently, the arylethylene (9) is reacted with paraformaldehyde ($CH_2O$). and hydrogen chloride in acetic On the other hand, the 3,7-bisbutadienylphenothiazines and 3,7-bisbutadienylphenoxazines (1d) represented by general formula (1) wherein $n=m=1$, $Ar^1=Ar^2$, and $R^1=R^2$ can be synthesized according to reaction scheme 7. Specifically, a 10-substituted 3,7-diformylphenothiazine or phenoxazine (2) is reacted with 2 mol of a 3-arylallylphosphonic acid dialkyl ester (7) per mol of compound (2) in the presence of a base to produce the target compound and this reaction can be carried out in the same manner as in the synthesis of compound (1a):

Reaction scheme 7

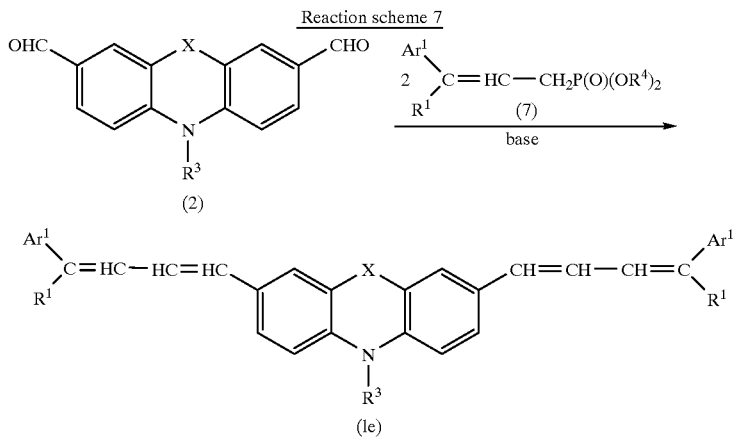

wherein $Ar^1$, $R^1$, $R^3$, and X have the same meanings as defined above, and $R^4$ represents a lower alkyl group.

The 3,7-bisbutadienylphenothiazines and 3,7-bisbutadienylphenoxazines (1e) represented by general formula (1) wherein $n=m=1$, $Ar^1$ and $Ar^2$ may be the same or different, and $R^1$ and $R^2$ may be the same or different can be synthesized according to reaction scheme 8:

Compound (12) is reacted with a 3-arylallylphosphonic acid dialkyl ester different from compound (7) used above, whereby the target compound (1e) according to the present invention can be synthesized.

When compound (1) of the present invention is used as a charge-transporting material, a high carrier mobility is

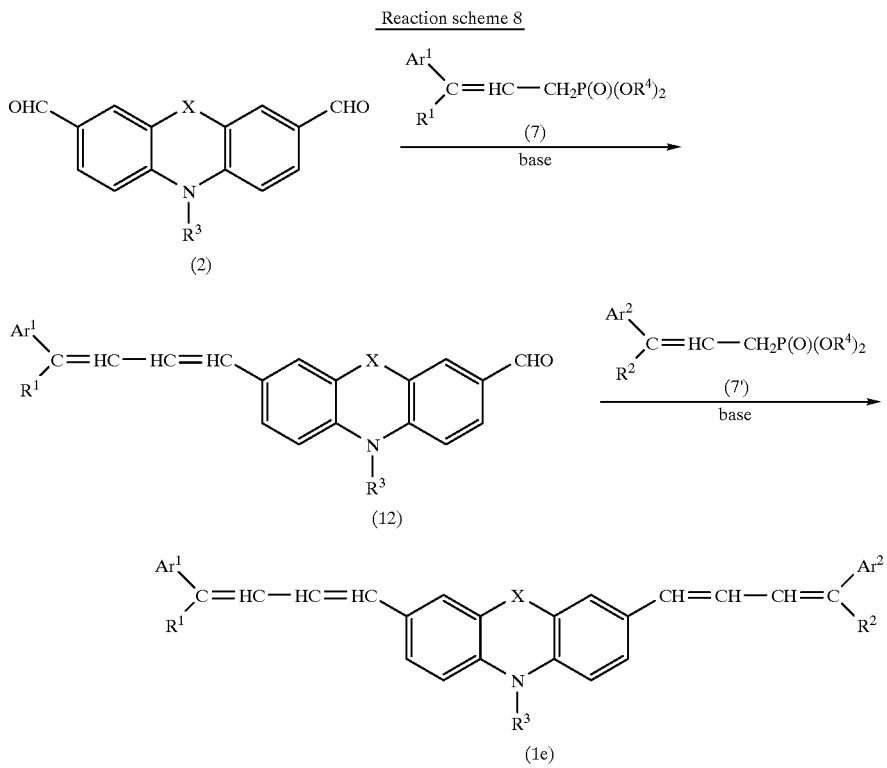

wherein $Ar^1$, $R^1$, $Ar^2$, $R^2$, $R^3$, and X have the same meanings as defined above, and $R^4$ represents a lower alkyl group.

Specifically, a diformylated compound (2) is reacted with an equimolar amount of a 3-arylallylphosphonic acid dialkyl ester (7) in the presence of a base to synthesize a 10-substituted 3-butadienyl-7-formylphenothiazine or 10-substituted 3-butadienyl-7-formylphenoxazine (12).

obtained and a high-sensitivity electrophotographic photoreceptor can be obtained.

Compound (1) of the present invention is also usable in a wide range of fields including organic electroluminescence (EL).

An example of the electrophotographic photoreceptor according to the present invention is a laminate type electrophotographic photoreceptor comprising a conductive support and, formed thereon, a charge-generating layer and a charge-transporting layer which layers perform their respective functions. In this photoreceptor, the charge-transporting layer comprises compound (1) of the present invention as a charge-transporting material.

Compound (1) of the present invention can also be utilized as a charge-transporting material for use in a single-layer electrophotographic photoreceptor containing in the same layer a charge-generating material and one or more charge-transporting materials comprising compound (1).

The charge-transporting layer comprising compound (1) of the present invention as a charge-transporting material is formed by vapor-depositing compound (1) as it is on a conductive support, or by dissolving compound (1) in an appropriate solvent together with a binder, applying the solution on a conductive support or a charge-generating layer, and drying the coating. On the other hand, the single-layer photoreceptor containing a charge generator and compound (1) of the present invention is obtained by dissolving or dispersing the charge generator and compound (1) in an appropriate solvent together with a binder, applying the solution on a conductive support, and drying the coating. A single-layer photoreceptor containing compound (1) of the present invention and an electron acceptor compound capable of forming a charge-transfer complex with compound (1) can be obtained in the same manner as the above.

Examples of the binder include polycarbonates, polyesters, polystyrene, polyacrylates, polymethacrylates, polyamides, acrylic resins, vinyl chloride resins, vinyl acetate resins, epoxy resins, polyurethanes, and copolymers thereof. Also usable besides such insulating polymers are organic photoconductive polymers such as polyvinylcarbazole, polyvinylanthracene, and polyvinylene.

Preferred of those binders are polycarbonates represented by general formula (F) below. Especially preferred examples thereof include bisphenol A type polycarbonates represented by formula (G) below (e.g., Yupilon E series, manufactured by Mitsubishi Gas Chemical Company, Inc., Japan) and bisphenol Z type polycarbonate resins represented by formula (H) below (e.g., Polycarbonate Z series, manufactured by Mitsubishi Gas Chemical Company, Inc.). Other usable polycarbonates are represented by formulae (I), (J), and (K) below. Also usable are copolymers each comprising two or more kinds of monomer units shown in formulae (G) to (K). Preferred among these copolymers are copolycarbonates containing biphenol carbonate units represented by formula (L) below. Specific examples of these copolycarbonates include bisphenol A/biphenol type copolycarbonate resins represented by formula (M) below (wherein n/(n+m) is preferably from 0.1 to 0.9, more preferably from 0.7 to 0.9):

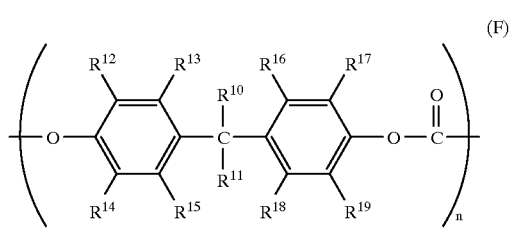

wherein $R^{10}$ and $R^{11}$ each independently represents a hydrogen atom, an alkyl group, or an aryl group, or $R^{10}$ and $R^{11}$ may be bonded to each other to form a ring; $R^{12}$, $R^{13}$, $R^{14}$, $R^{15}$, $R^{16}$, $R^{17}$, $R^{18}$, and $R^{19}$ each independently represents a hydrogen atom, a halogen atom, an alkyl group, or an aryl group; and n indicates an integral number of the repeating units;

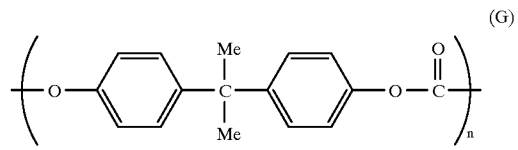

bisphenol A type polycarbonate wherein n indicates an integral number of the repeating units;

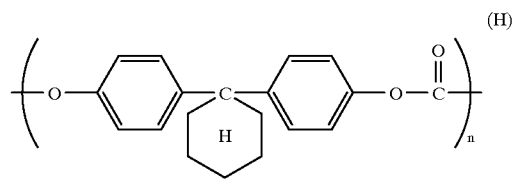

bisphenol Z type polycarbonate wherein n indicates an integral number of the repeating units;

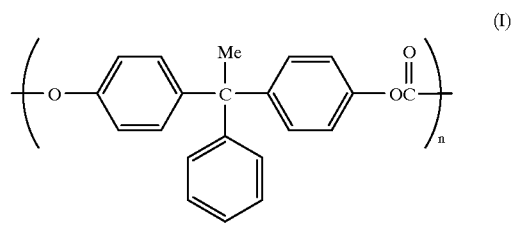

wherein n indicates an integral number of the repeating units;

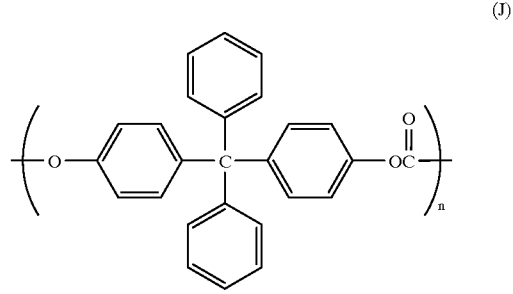

wherein n indicates an integral number of the repeating units;

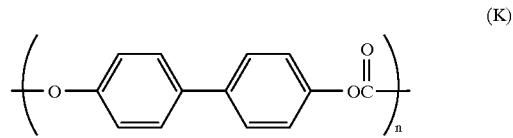

wherein n indicates an integral number of the repeating units;

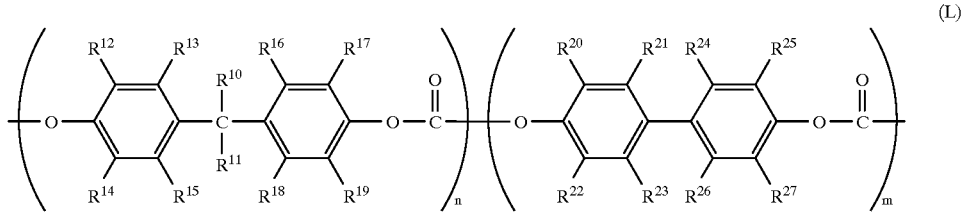

bisphenol copolycarbonate wherein $R^{10}$ and $R^{11}$ each independently represents a hydrogen atom, an alkyl group, or an aryl group, or $R^{10}$ and $R^{11}$ may be bonded to each other to form a ring; $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ each independently represents a hydrogen atom, a halogen atom, an alkyl group, or an aryl group; and m and n each indicates an integral number of the repeating units; and

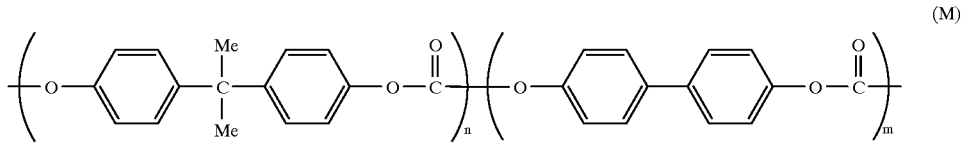

bisphenol A/biphenol type polycarbonate resin wherein n and m each indicates an integral number of the repeating units; n/(n+m) is from 0.1 to 0.9.

Also usable besides the polycarbonates described above is the polycarbonate disclosed in JP-A-6-214412 which has repeating units represented by the following structural formula.

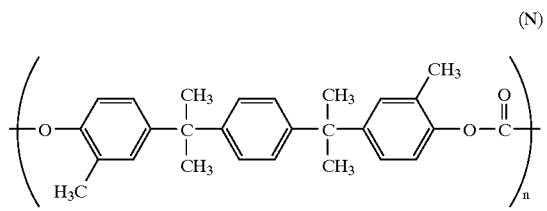

wherein n indicates an integral number of the repeating units.

Furthermore, the polycarbonates disclosed in JP-A-6-222581 which are represented by the following structural formula can be used.

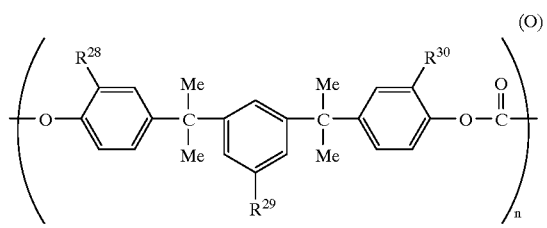

wherein $R^{28}$, $R^{29}$, and $R^{30}$ may be the same or different and each represents a hydrogen atom, a halogen atom, an alkyl group, a cycloalkyl group, an aryl group, or an arylalkyl group, and n indicates an integral number of the repeating units.

The proportion of such a binder to compound (1) of the present invention may be such that the amount of the charge-transporting material is from 10 to 1,000 parts by weight, preferably from 30 to 500 parts by weight, more preferably from 40 to 200 parts by weight, per 100 parts by weight of the binder. An organic solvent is used without any particular limitation. Examples of the solvent include alcohols such as methanol, ethanol, and isopropanol, ketones such as acetone, methyl ethyl ketone, and cyclohexanone, amides such as N,N-dimethylformamide and N,N-dimethylacetamide, sulfoxides such as dimethyl sulfoxide, ethers such as tetrahydrofuran, dioxane, and ethylene glycol dimethyl ether, esters such as ethyl acetate and methyl acetate, halogenated aliphatic hydrocarbons such as methylene chloride, chloroform, 1,2-dichloroethane, dichloroethylene, trichloroethylene, trichloroethane, and carbon tetrachloride, and aromatic compounds such as toluene, xylene, chlorobenzene, and dichlorobenzene. These solvents may be used alone or as a mixture thereof.

The conductive support used in the photoreceptor of the present invention may be a foil or plate of a metal, e.g., copper, aluminum, silver, iron, zinc, or nickel, or of an alloy thereof. These materials are used in a sheet or drum form. Also usable as the conductive support is one obtained by depositing any of these metals on a plastic film or cylinder or the like by vacuum deposition or electroplating, or one obtained by forming a layer of a conductive compound, e.g., a conductive polymer, indium oxide, or tin oxide, on a sheet- or drum-form support made of, e.g., glass, paper, or a plastic by coating or vapor deposition.

The coating may be conducted by using any of coating techniques such as dip coating, spray coating, spinner coating, wire-wound bar coating, blade coating, roller coating, and curtain coating.

In a preferred drying method, the coating layer is dried first at room temperature and then with heating. In general, the drying with heating is preferably conducted at a temperature of 30° to 200° C. for 5 minutes to 2 hours with or without air blowing.

If desired and necessary, other charge-transporting materials and various additives may be further incorporated into the charge-transporting layer in the present invention. Examples of usable other charge-transporting materials include the hydrazone compounds represented by the following general formula (I), which are described, e.g., in JP-B-55-42380 (the term "JP-B" as used herein means an "examined Japanese patent publication"), JP-A-60-340999, and JP-A-61-23154), the triphenylamine dimers represented by the following general formula (II), which are described, e.g., in JP-B-58-32372, and the distyryl compounds represented by the following general formula (III), which are described, e.g., in U.S. Pat. No. 3,873,312. Examples thereof further include tetraphenylbutadiene compounds, α-phenylstilbene, polyvinylcarbazole, and triphenylmethane. However, the charge-transporting materials optionally usable in the present invention are not limited to these examples.

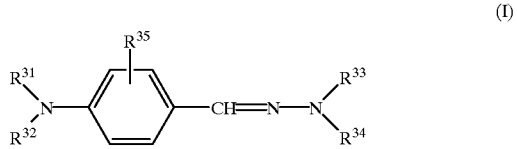
(I)

wherein $R^{31}$ and $R^{32}$ may be the same or different, and each represents an optionally substituted lower alkyl group, an optionally substituted aryl group, or an optionally substituted aralkyl group. $R^{33}$ and $R^{34}$ may be the same or different, and each represents an optionally substituted lower alkyl group, an optionally substituted aryl group, an optionally substituted aralkyl group, or an optionally substituted heterocyclic group, or $R^{33}$ and $R^{34}$ may be bonded to each other to form a ring. $R^{35}$ represents a hydrogen atom, a lower alkyl group, an optionally substituted aryl group, an optionally substituted aralkyl group, a lower alkoxy group, or a halogen atom. $R^{35}$ may be bonded to $R^{31}$ or $R^{32}$ to form a ring.

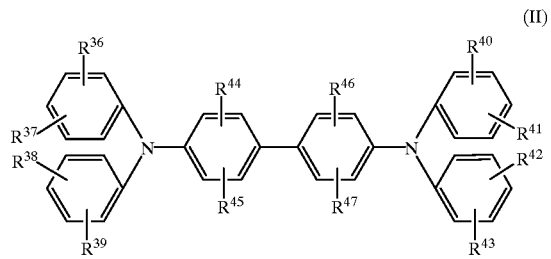
(II)

wherein $R^{36}$ to $R^{47}$ may be the same or different, and each represents a hydrogen atom, a lower alkyl group, a lower alkoxy group, a halogen-substituted lower alkoxy group, an optionally substituted aryl group, or a halogen atom.

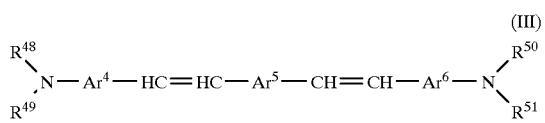
(III)

$R^{48}$ to $R^{51}$ may be the same or different, and each represents a lower alkyl group or an optionally substituted aryl group. $Ar^4$ and $Ar^6$ may be the same or different, and each represents a phenylene group which may have one or more substituents selected from the group consisting of a lower alkyl group, a lower alkoxy group, an aryloxy group, and a halogen atom. $Ar^5$ represents a mono- or polycyclic aromatic group which has 4 to 14 carbon atoms and may have the same substituents as $Ar^4$ and $Ar^6$, or represents a heterocycle which may have the same substituents as $Ar^4$ and $Ar^6$.

Examples of the various additives include plasticizers such as the biphenyl compounds disclosed in JP-A-6-332206, m-terphenyl, and dibutyl phthalate, surface lubricants such as silicone oil, graft type silicone polymers, and various fluorocarbons, potential stabilizers such as dicyanovinyl compounds and carbazole derivatives, monophenol type antioxidants such as 2-tert-butyl-4-methylphenol and 2,6-di-tert-butyl-4-methylphenol, bisphenol type antioxidants, amine type antioxidants such as 4-diazabicyclo [2.2.2]octane, salicylic acid type antioxidants, and tocopherol.

The thickness of the charge-transporting layer obtained is from 5 to 40 μm, preferably from 10 to 30 μm.

The thus-obtained charge-transporting layer is electrically connected to a charge-generating layer. As a result, the charge-transporting layer can have the functions of receiving carriers injected from the charge-generating layer in the presence of an electric field and transporting the carriers to the photoreceptor surface. In this case, the charge-transporting layer may overlie the charge-generating layer or underlie it, but desirably overlies the charge-generating layer.

On the photosensitive layer thus formed, a protective layer may be formed by coating if desired and necessary. Further, an undercoat layer which has a barrier function and an adhesive function may also be provided between the conductive support and the photosensitive layer. Examples of materials which can be used for forming an undercoat layer include polyvinyl alcohol, nitrocellulose, casein, ethylene-acrylic acid copolymers, polyamides such as nylon, polyurethanes, gelatin, and aluminum oxide. The thickness of the undercoat layer is usually from 0.1 to 5 μm, preferably from 0.5 to 3 μm.

For forming the charge-generating layer, use may be made of one or more materials selected from inorganic charge-generating materials, e.g., selenium, selenium-tellurium, and amorphous silicon, and organic charge-generating substances, e.g., cationic dyes such as pyrylium salt dyes, thiapyrylium salt dyes, azulenium salt dyes, thiacyanine dyes, and quinocyanine dyes, squarylium salt pigments, phthalocyanine pigments, polycyclic quinone pigments such as anthanthrone pigments, dibenzpyrenequinone pigments, and pyranthrone pigments, indigo pigments, quinacridone pigments, azo pigments, and pyrrolopyrrole pigments. These materials may be used alone or in combination to form a layer thereof by vapor deposition or coating.

Especially preferred among the organic charge-generating substances enumerated above are the organic charge-generating substances described in Chem. Rev., 1993, 93, pp. 449–486.

Specific examples of the phthalocyanine pigments include alkoxytitanium phthalocyanine (Ti(OR)$_2$Pc), oxotitanium phthalocyanine (TiOPc), copper phthalocyanine (CuPc), metal-free phthalocyanine (H$_2$Pc), hydroxygallium phthalocyanine (HOGaPc), vanadyl phthalocyanine (VOPc), and chloroindium phthalocyanine (ClInPc). More specifically, examples of the TiOPc include α-TiOPc, β-TiOPc, γ-TiOPc, m-TiOPc, Y-TiOPc, A-TiOPc, B-TiOPc, and amorphous TiOPc, and examples of the H$_2$PC include α-H$_2$Pc, β-H$_2$Pc, τ-H$_2$Pc, and x-H$_2$Pc.

Two or more of these phthalocyanines may be mixed with each other by milling and used as a mixture or as a new mixed-crystal system. For example, use may be made of an oxotitanyl phthalocyanine/vanadyl phthalocyanine mixed crystal described, e.g., in JP-A-4-371962, JP-A-5-2278, and JP-A-5-2279 and an oxotitanyl phthalocyanine/chloroindium phthalocyanine mixed crystal described, e.g., in JP-A-6-148917, JP-A-6-145550, JP-A-6-271786, and JP-A-5-297617.

Preferred azo compounds are represented by the following structural formulae.

Bisazo Compounds

Cp$^1$—N≡N—A—N≡N—Cp$^2$

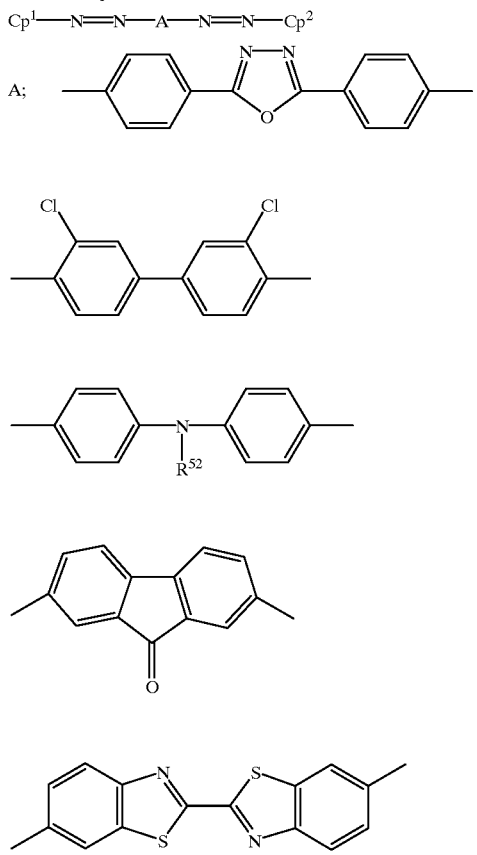

wherein R$^{52}$ represents a lower alkyl group.

Trisazo Compounds

Cp$^1$—N≡N—A—N≡N—Cp$^2$
           |
           N≡N—Cp$^3$

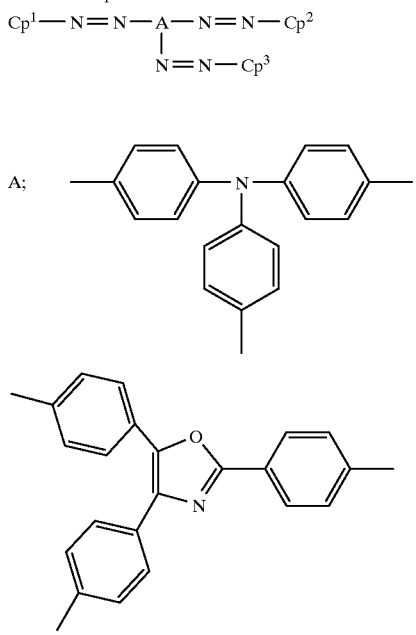

Cp$^1$ and Cp$^2$ in the bisazo compounds and Cp$^1$, Cp$^2$, and Cp$^3$ in the trisazo compounds each represents any of the following.

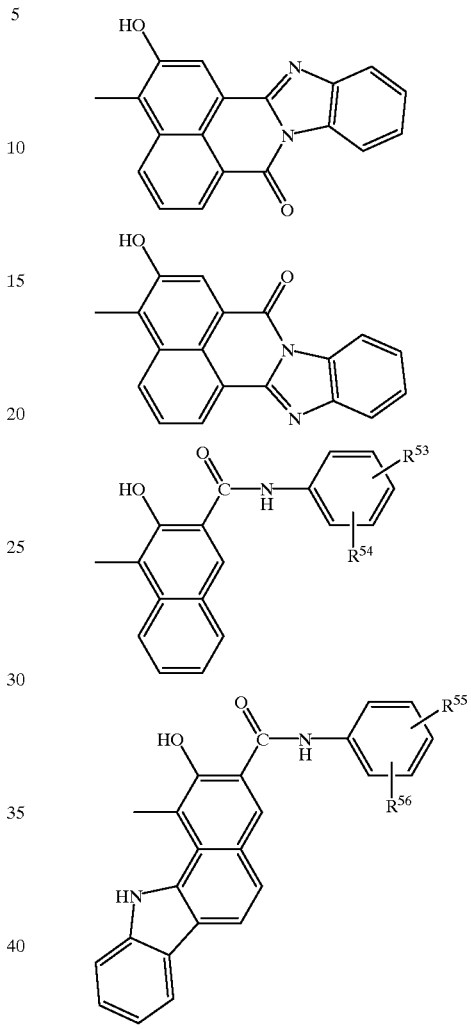

wherein R$^{53}$, R$^{54}$, R$^{55}$, and R$^{56}$ may be the same or different, and each represents a hydrogen atom, a halogen atom, or a lower alkyl group.

The perylene or polycyclic quinone compounds represented by the following structural formulae are also preferred.

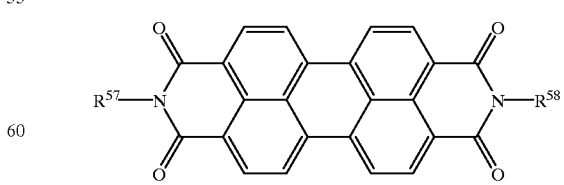

wherein R$^{57}$ and R$^{58}$ each represents a hydrogen atom, a lower alkyl group, or an aryl group.

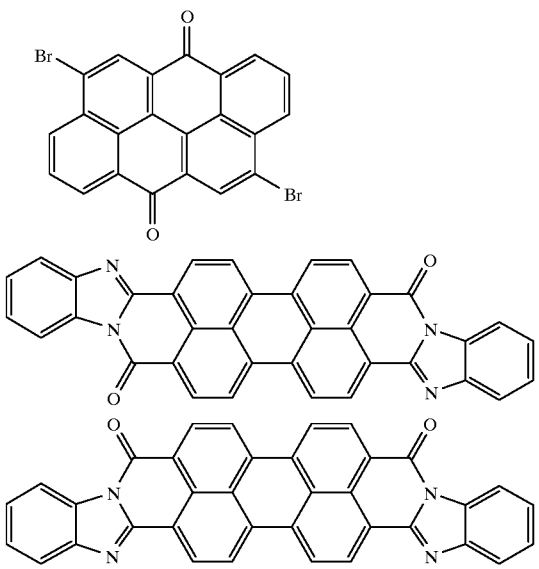

Besides those substances, any material can be used as long as it generates charges at a high efficiency upon light absorption.

Thus, an electrophotographic photoreceptor can be obtained which has a charge-transporting layer comprising the phenothiazine or phenoxazine derivative (1) of the present invention.

As described above, the phenothiazine or phenoxazine derivative (1) of the present invention, such as the compounds enumerated in Tables 1 to 4, gives a stable film and is excellent in various properties when used in an electrophotographic photoreceptor.

The present invention will be explained below in more detail by reference to the following Examples, but the invention should not be construed as being limited thereto. The analytical instruments and conditions shown below were used in the Examples.

(1) $^1$H-NMR

Instrument: Type AM-400 (400 MHz), manufactured by Bruker, Inc.

Solvent: $CDCl_3$ or $C_6D_6$

Internal reference: tetramethylsilane (2) MASS

Instrument: Hitachi M-80B (manufactured by Hitachi Ltd., Japan)

EXAMPLE 1

Synthesis of 3,7-Bis(2',2'-diphenylvinyl)-10-ethylphenothiazine (Exemplified Compound 4; n=m=0, X=S, $Ar^1$=$R^1$=$Ar^2$=$R^2$=Ph, $R^3$=ethyl)

(1) Synthesis of 10-Ethylphenothiazine (4a)

Into a 1-liter reaction flask were introduced 25 g (0.126 mol) of phenothiazine, 50.0 g (0.757 mol) of 85% KOH, 4.3 g (0.013 mol) of tetra-n-butylammonium hydrogensulfate, 28.0 g (0.203 mol) of potassium carbonate, and 500 ml of toluene. Thereto was gradually added 39.0 g (0.250 mol) of ethyl iodide. The mixture was reacted at 60° to 70° C. for 5 hours and then filtered. The filtrate was washed twice with water, dried with magnesium sulfate, and then concentrated. As a result, 28.7 g of a crude reaction product was obtained. This crude product was recrystallized from 100 ml of isopropanol to obtain 23.99 g of 10-ethylphenothiazine (4a). Yield, 84.1%; m.p., 104°–105° C.

(2) Synthesis of 3,7-Diformyl-10-ethylphenothiazine (2a)

To a mixture of 6.5 g (47.7 mmol) of dehydrated zinc chloride and 150 ml of toluene were added 14 ml (180.1 mmol) of N,N-dimethylformamide (DMF) and 10.0 g (44.0 mmol) of 10-ethylphenothiazine (4a). Thereto was gradually added dropwise 27.0 g (176.1 mmol) of phosphorus oxychloride at room temperature to 35° C. The resultant mixture was reacted at 73° to 78° C. for 3 days and then poured into 200 ml of water. This mixture was neutralized with sodium carbonate, stirred at 80° C. for 3 hours, and then subjected to liquid separation. The aqueous layer was extracted with ethyl acetate three times, and the resultant organic layer collected was dried with magnesium sulfate and concentrated. The residue was recrystallized from an isopropanol/ethyl acetate mixed solvent to obtain 4.96 g of 3,7-diformyl-10-ethylphenothiazine (2a). Yield, 58.7%; m.p., 132°–145° C. MS: 284 ($M^+$), 283, 268, 254, 236, 226, 198, 154. $^1$H-NMR (δ; ppm in $CDCl_3$): 1.50 (t, J=7.0.Hz, 3H), 4.00 (q, J=7.0 Hz, 2H), 6.96 (d, J=8.5 Hz, 2H), 7.58 (s, 2H), 7.65 (d, J=8.5 Hz, 2H), 9.85 (s, 2H).

(3) Synthesis of 3,7-Bis(2',2'-diphenylvinyl)-10-ethylphenothiazine (Exemplified Compound 4)

In 20 ml of DMF were dissolved 2.0 g (7.1 mmol) of 3,7-diformyl-10-ethylphenothiazine (2a) and 4.7 g (15.5 mmol) of diethyl diphenylmethylphosphonate (3a). Thereto was gradually added 2.0 g (17.8 mmol) of potassium t-butoxide. The mixture was reacted at room temperature overnight and then poured into 100 ml of methanol. The resultant precipitate was taken out by filtration, dissolved in toluene, and purified by silica gel column chromatography (eluent: toluene/hexane=1/1). This reaction product was recrystallized from an ethyl acetate/ethanol mixed solvent to obtain 1.58 g of Exemplified Compound 4. Yield, 38.3%; m.p., 122°–123° C. MS: 583 ($M^+$), 554, 527, 292. $^1$H-NMR (δ; ppm in $C_6D_6$): 0.79 (t, J=7.0 Hz, 3H), 3.10 (q, J=7.0 Hz, 2H), 6.17 (d, J=8.5 Hz, 2H), 6.77 (dd, J=8.5 Hz, J=2.1 Hz, 2H), 6.79 (s, 1H), 6.83 (d, J=2.1 Hz, 2H), 7.05–7.18 (m, 12H), 7.20 (m, 4H), 7.32 (m, 4H).

EXAMPLE 2

Synthesis of 3,7-Bis(4',4'-diphenylbutadienyl)-10-ethylphenothiazine (Exemplified Compound 12; n=m=1, X=S, $Ar^1$=$R^1$=$Ar^2$=$R^2$=Ph, $R^3$=ethyl)

(1) Synthesis of 1,1-Diphenylethylene (9a)

Into a 2-liter reaction flask were introduced in a nitrogen stream 31.6 g (1.3 mol) of magnesium and 50 ml of dry THF. Slight amounts of iodine and ethyl bromide were further added, following which the initiation of reaction was ascertained. Subsequently, 600 ml of dry THF was added with stirring, and methyl chloride gas was bubbled into the mixture. The reaction mixture was maintained at 30° to 40° C. by controlling both the amount of the gas being bubbled and cooling. Heat generation ended in 2 hours with the disappearance of the magnesium. The bubbling of methyl chloride gas was then stopped and the mixture was stirred at that temperature for 1 hour to complete the preparation of a Grignard reagent.

To this reaction mixture was added dropwise a liquid mixture of 182.2 g (1.1 mol) of benzophenone (8a; Ar=R=Ph) and 365 ml of dry THF at 35° to 40° C. over a period of 30 minutes. This mixture was stirred at that temperature for 2 hours and for further 13 hours to complete the reaction. The reaction mixture was poured into 1.4 kg of cooled 10% aqueous ammonium chloride solution with cooling with ice. This mixture was stirred for 30 minutes, allowed to stand, and then subjected to liquid separation, followed by washing with aqueous common salt solution, drying with magnesium sulfate, and concentration to obtain 200.2 g of a crude carbinol (theoretical yield based on the benzophenone, 98.6%). Into a 1-liter reaction flask were introduced 200.2 g of the crude carbinol, 400 ml of toluene, and 1 g of p-toluenesulfonic acid (PTSA). Azeotropic dehydration was conducted for 2 hours with toluene refluxing (94°–116° C.). After cooling, this reaction mixture was washed with water, with 2% aqueous soda ash solution, and then with water, dried with magnesium sulfate, and concentrated to obtain 190.1 g of crude 1,1-diphenylethylene. This crude reaction product was distilled with a Claisen flask equipped with a vigreux to obtain 174.1 g of 1,1-diphenylethylene (9a; Ar=R=Ph). b.p., 103° C./1 mmHg.

The yield based on the benzophenone was 96.5%.

(2) Synthesis of 3,3-Diphenylallyl Chloride (11a; Ar=R=Ph)

Into a 300-ml reaction flask were introduced 54.1 g (0.3 mol) of 1,1-diphenylethylene (9a), 108.26 g of acetic acid, and 13.5 g (0.45 mol) of paraformaldehyde. Hydrogen chloride in an amount of 13.67 g (0.375 mol) was then bubbled into the mixture with stirring at 30° C. over a period of 3.5 hours, during which the reaction mixture was cooled and kept at 30° C. because slight heat generation occurred. After the bubbling of hydrogen chloride was stopped, the reaction mixture was stirred at that temperature for 2 hours and then allowed to stand overnight. The resulting reaction mixture was poured into 200 ml of water and extracted with 200 ml of toluene. The extract was washed with water, with 2% soda ash solution, and then with water, dried with magnesium sulfate, and concentrated to obtain 68.4 g of a crude chloride. This crude chloride was distilled with a Claisen flask equipped with a vigreux to obtain 57.5 g of the target compound.

b.p., 120°–132° C./1 mmHg. Yield, 79%. MS: 228 (M+), 193, 178, 115. $^1$H-NMR (δ; ppm in $CDCl_3$): 4.11 (2H, d, J=8.0 Hz), 6.23 (1H, t, J=8.0 Hz), 7.21–7.41 (10H, m).

(3) Synthesis of Diethyl 3,3-Diphenylallylphosphonate (7a; Ar=R=Ph, $R^4$=ethyl)

A mixture of 40.8 g (0.155 mol) of 3,3-diphenylallyl chloride (11a) and 94.48 g (0.569 mol) of triethyl phosphite was stirred with refluxing for 24 hours. The disappearance of the 3,3-diphenylallyl chloride (11a) was ascertained, before the reaction was terminated. After cooling, the reaction mixture was distilled with a Claisen flask equipped with a vigreux to obtain 55.39 g of the target compound.

b.p., 170°–203° C./1 mmHg. Theoretical yield, 99%. MS: 330 (M+), 193, 115. $^1$H-NMR (δ; ppm in $CDCl_3$): 1.31 (6H, t, J=7.0 Hz), 2.71 (2H, dd, J=7.9 Hz, J=22.4 Hz), 4.08 (6H, dt, J=7.1 Hz, J=7.6 Hz), 6.12 (1H, q, J=7.9 Hz, J=7.6 Hz), 7.22–7.38 (10H, m).

(4) Synthesis of 3,7-Bis(4',4'-diphenylbutadienyl)-10-ethylphenothiazine (Exemplified Compound 12)

In 20 ml of DMF were dissolved 1.6 g (5.7 mmol) of 3,7-diformyl-10-ethylphenothiazine (2a)-and 4.1 g (12.4 mmol) of diethyl 3,3-diphenylallylphosphonate (7a). Thereto was gradually added 1.5 g (13.4 mmol) of potassium t-butoxide at room temperature. The mixture was stirred at that temperature overnight and then poured into 50 ml of methanol. The resultant precipitate was taken out by filtration and purified by silica gel column chromatography (eluent: hexane/toluene=1/1) to obtain 2.38 g of the target reaction product. This reaction product was recrystallized from an ethyl acetate/ethanol mixed solvent to obtain 1.47 g of Exemplified Compound 12.

Yield, 40.9%; m.p., 183°–184° C. MS: 635 (M+), 606, 191, 43. $^1$H-NMR (δ; ppm in $C_6D_6$): 0.90 (t, J=7.0 Hz, 3H), 3.25 (q, J=7.0 Hz, 2H), 6.28 (d, J=8.5 Hz, 2H), 6.51 (d, J=15.4 Hz, 2H), 6.89 (d, J=11.1 Hz, 2H), 6.92 (dd, J=8.5 Hz, J=1.9 Hz, 2H), 7.02 (d, J=11.1 Hz, 2H), 7.05–7.21 (m, 14H), 7.28 (m, 4H), 7.37 (m, 4H).

EXAMPLE 3

Synthesis of 3,7-Bis(2',2'-diphenylvinyl)-10-p-tolylphenothiazine (Exemplified Compound 22; n=m=0, X=S, $Ar^1$=$R^1$=$Ar^2$=$R^2$=Ph, $R^3$=p-tolyl)

(1) Synthesis of 10-p-Tolylphenothiazine (4b)

A mixture of 25 g (0.126 mol) of phenothiazine, 33 g (0.151 mol) of p-iodotoluene, 4 g (0.025 mol) of copper sulfate, 23 g of potassium carbonate, and 200 ml of diisopropylbenzene was reacted at 180° C. for 3 hours and then at 200° C. for 1 day. The mixture was then cooled and filtered through a Celite. The filtrate was concentrated, and the residual crystals were recrystallized from an ethanol/ethyl acetate mixed solvent to obtain 27.5 g of 10-p-tolylphenothiazine (4b).

Yield, 75.7%; m.p., 134° C. MS (direct): 289 (M+), 273, 257, 241, 198, 166, 154. $^1$H-NMR ($CDCl_3$): 2.05 (s, 3H), 6.23 (d, J=7.8 Hz, 2H), 6.57–6.68 (m, 4H), 6.95 (d, J=7.3 Hz, 2H), 6.92 (s, 4H).

(2) Synthesis of 3,7-Diformyl-10-p-tolylphenothiazine (2b)

To 200 ml of toluene were added 20.0 g (69.1 mmol) of 10-p-tolylphenothiazine (4b), 10.0 g (73.4 mmol) of zinc chloride, and 22 ml (284.1 mmol) of DMF. The mixture was stirred, and 27 ml (289.7 mmol) of phosphorus oxychloride was gradually added thereto dropwise. The resultant mixture was reacted at 80° C. for 3 days and then poured into 300 ml of water. This mixture was neutralized with sodium carbonate, stirred at 80° C. for 2 hours, and then subjected to liquid separation. The aqueous phase was extracted with toluene three times, and the resultant organic phase collected was dried (with $MgSO_4$) and concentrated. The residue was recrystallized twice from ethyl acetate to obtain 8.59 g of the target compound.

Yield, 40.0%; m.p., 215°–217° C. MS (Direct): 345 (M+); 316, 288. $^1$H-NMR ($CDCl_3$): 2.50 (s, 3H), 6.20 (d, J=8.5 Hz, 2H), 7.24 (d, J=8.2 Hz, 2H), 7.29 (dd, J=8.6 Hz, J=1.9 Hz, 2H), 7.45 (d, J=1.9 Hz, 2H), 7.48 (d, J=8.4 Hz, 2H), 9.71 (s, 2H).

(3) Synthesis of 3,7-Bis(2',2'-diphenylvinyl)-10-p-tolylphenothiazine (Exemplified Compound 22)

In 20 ml of DMF were dissolved 2.0 g (5.8 mmol) of 3,7-diformyl-10-p-tolylphenothiazine (2b) and 4.0 g (13.2 mmol) of diethyl diphenylmethylphosphonate (3a). Thereto was gradually added 1.5 g (13.4 mmol) of potassium t-butoxide. After the mixture was reacted overnight, 10 ml of methanol was added thereto. The crystals precipitated were taken out by filtration, dissolved in chloroform, purified by silica gel column chromatography (toluene), and then recrystallized from a chloroform/hexane mixed solvent to obtain 1.48 g of the target compound.

Yield, 39.6%; m.p., 265°–268° C. MS (Direct): 645 (M+); 83. $^1$H-NMR ($CDCl_3$): 2.39 (s, 3H), 5.80 (d, J=6.2 Hz, 2H), 6.38 (d, J=7.9 Hz, 2H), 6.58 (brs, 2H), 6.73 (brs, 2H), 7.11–7.18 (m, 6H), 7.21–7.36 (m, 18H).

EXAMPLE 4

Synthesis of 3,7-Bis(4',4'-diphenylbutadienyl)-10-p-tolylphenothiazine (Exemplified Compound 23; n=m=1, X=S, $Ar^1$=$R^1$=$Ar^2$=$R^2$=Ph, $R^3$=p-tolyl)

In 20 ml of DMF were dissolved 1.5 g (4.3 mmol) of 3,7-diformyl-10-p-tolylphenothiazine (2b) and 3.6 g (10.9 mmol) of diethyl 3,3-diphenylallylphosphonate (7a). Thereto was gradually added 1.3 g of potassium t-butoxide.

After the mixture was reacted overnight, 100 ml of methanol was added thereto. The crystals precipitated were taken out by filtration, purified by silica gel column chromatography (toluene/hexane=1/1), and then recrystallized from a toluene/hexane mixed solvent to obtain 2.29 g of the target compound.

Yield, 75.7%; m.p., 247°–249° C. MS (Direct): 697 (M$^+$); 493, 269, 169, 129. $^1$H-NMR (CDCl$_3$): 2.10 (s, 3H), 5.97 (d, J=8.6 Hz, 2H), 6.42 (d, J=15.2 Hz, 2H), 6.61 (dd, J=8.7 Hz, J=2.0 Hz, 2H), 6.81 (d, J=8.2 Hz, 2H), 6.85 (d, J=11.2 Hz, 2H), 6.90–7.00 (m, 6H), 7.04–7.20 (m, 12H), 7.27 (m, 4H), 7.34 (m, 4H).

EXAMPLE 5

Synthesis of 3,7-Bis(2',2'-diphenylvinyl)-10-ethylphenoxazine (Exemplified Compound 58; n=m=0, X=O, Ar$^1$=R$^1$=Ar$^2$=R$^2$=Ph, R$^3$=ethyl)

(1) Synthesis of 10-Ethylphenoxazine (4c)

Into a reaction flask were introduced 3.0 g (16.4 mmol) of phenoxazine, 6.5 g (98.5 mmol) of 85% KOH, 3.7 g (26.8 mmol) of potassium carbonate, 577 mg (1.7 mmol) of tetra-n-butylammonium hydrogensulfate, and 100 ml of toluene. Thereto was gradually added 5.1 g (32.7 mmol) of ethyl iodide with a dropping funnel (slight heat generation occurred). Subsequently, the mixture was reacted at 60° to 80° C. for 7 hours. After the disappearance of the phenoxazine was ascertained by TLC and gas chromatography, the resultant toluene solution was cooled, washed with water three times, dried (with MgSO$_4$), and then concentrated. The residue was distilled under vacuum to obtain 2.72 g of 10-ethylphenoxazine.

Yield, 78.7%; b.p., 120°–122° C./ 1 mmHg. MS: 211 (M$^+$); 196, 182. $^1$H-NMR (δ; ppm in C$_6$D$_6$): 0.73 (t, J=7.1 Hz, 3H), 2.98 (q, J=7.1 Hz, 2H), 6.14 (d, J=7.9 Hz, 2H), 6.51 (dt, J=7.6 Hz, 2H), 6.64 (t, J=7.6 Hz, 2H), 6.70 (d, J=7.7 Hz, 2H).

(2) Synthesis of 3,7-Diformyl-10-ethylphenoxazine (2c)

Reaction was conducted using 2.7 g (12.8 mmol) of 10-ethylphenoxazine (4c), 3.8 g (52.0 mmol) of DMF, 1.8 g (13.2 mmol) of zinc chloride, 7.8 g (50.9 mmol) of phosphorus oxychloride, and 50 ml of toluene in the same manner as in Example 1 (2). The resultant reaction mixture was treated in the same manner to obtain 2.47 g of 3,7-diformyl-10-ethylphenoxazine (2c).

Yield, 72.3%; m.p., 199°–200° C. MS: 267 (M$^+$); 252, 238, 224, 210, 182. $^1$H-NMR (δ; ppm in CDCl$_3$): 1.35 (t, J=7.2 Hz, 3H), 3.72 (q, J=7.2 Hz, 2H), 6.64 (d, J=8.3 Hz, 2H), 7.13 (d, J=1.8 Hz, 2H), 7.37 (dd, J=8.2 Hz, H=1.8 Hz, 2H), 9.71 (s, 2H).

(3) Synthesis of 3,7-Bis(2',2'-diphenylvinyl)-10-ethylphenoxazine (Exemplified Compound 58)

In 20 ml of DMF were reacted 1.2 g (4.5 mmol) of 3,7-diformyl-10-ethylphenoxazine (2c), 3.5 g (11.5 mmol) of diethyl diphenylmethylphosphonate (3a), and 1.3 g of potassium t-butoxide in the same manner as in Example 1 (3). The reaction mixture was poured into methanol. The resultant precipitate was purified by silica gel column chromatography (eluent: toluene/hexane=1/1) and then recrystallized from ethyl acetate to obtain 1.91 g of Exemplified Compound 58.

Yield, 74.9%; m.p., 216°–217° C. MS: 567 (M$^+$); 532, 283. $^1$H-NMR (δ; ppm in C$_6$D$_6$): 0.55 (t, J=7.0 Hz, 3H), 2.75 (q, J=7.2 Hz, 2H), 5.81 (d, J=8.4 Hz, 2H), 6.44 (d, J=2.0 Hz, 2H), 6.52 (dd, J=8.4 Hz, J=2.1 Hz, 2H), 6.79 (s, 2H), 7.06–7.19 (m, 12H), 7.25 (m, 4H), 7.32 (m, 4H).

EXAMPLE 6

Synthesis of 3,7-Bis(4',4'-diphenylbutadienyl)-10-ethylphenoxazine (Exemplified Compound 66; n=m=1, X=O, Ar$^1$=R$^1$=Ar$^2$=R$^2$=Ph, R$^3$=ethyl)

Reaction was conducted using 1.23 g (4.6 mmol) of 3,7-diformyl-10-ethylphenoxazine (2c), 3.4 g (10.3 mmol) of diethyl 3,3-diphenylallylphosphonate (7a), 20 ml of DMF, and 1.5 g (13.4 mmol) of potassium t-butoxide in the same manner as in Example 2 (4). The resultant reaction mixture was treated in the same manner to obtain 1.90 g of Exemplified Compound 66.

Yield, 66.5%; m.p., 205°–207° C. MS: 619 (M$^+$), 590, 564. $^1$H-NMR (δ; ppm in C$_6$D$_6$): 0.69 (t, J=7.0 Hz, 3H), 2.86 (q, J=7.1 Hz, 2H), 6.53 (d, J=15.3 Hz, 2H), 6.67 (dd, J=8.4 Hz, J=1.9 Hz, 2H), 6.73 (d, J=1.9 Hz, 2H), 6.90 (d, J=11.1 Hz, 2H), 7.00–7.22 (m, 16H), 7.30 (m, 4H), 7.37 (m, 4H).

SYNTHESIS EXAMPLE 1

Synthesis of 2,7-Bis(2',2'-diphenylvinyl)xanthene (Comparative Compound 1; relating to JP-A-6-271846)

(1) Synthesis of 2,7-Dibromoxanthene

In 100 ml of chloroform was dissolved 5.0 g (27.4 mmol) of xanthene. Thereto was gradually added 3.0 ml (58.2 mmol) of bromine. The mixture was stirred at room temperature for 3 days and then concentrated. The concentrate was recrystallized twice from chloroform to obtain 3.55 g of 2,7-dibromoxanthene.

Yield, 38.1 %; m.p., 174°–176° C. $^1$H-NMR (CDCl$_3$): 3.99 (s, 2H), 6.91 (d, J=9.1 Hz, 2H), 7.26–7.31 (m, 4H). MS (direct): 340 (M$^+$); 259, 232, 180, 152, 126.

(2) Synthesis of 2,7-Bis(2',2'-diphenylvinyl)xanthene

A Grignard reagent solution was prepared from 5.8 g (22.4 mmol) of 2,2-diphenyl-1-bromoethylene, 816 mg (33.6 milligram equivalents) of magnesium, and 30 ml of THF. In 10 ml of THF were suspended 3.0 g (8.8 mmol) of 2,7-dibromoxanthene and 150 mg (0.28 mmol) of bis(1,3-diphenylphosphinopropane)nickel chloride (NiCl$_2$DPPP). To this suspension was dropwise added the Grignard reagent solution. The mixture was refluxed for 3 days and then poured into an aqueous ammonium chloride solution. The resultant mixture was subjected to filtration through a Celite, extraction with toluene, drying (with MgSO4), and concentration. The residue was separated by silica gel column chromatography (eluent: toluene/hexane=1/3) to obtain 650 mg of a crude reaction product. This crude product was recrystallized twice from an ethanol/methylene chloride mixed solvent to obtain 600 mg of the target compound.

Yield, 12.6%; m.p., 173°–174° C. $^1$H-NMR (CDCl$_3$): 3.64 (s, 2H), 6.70–6.81 (m, 6H), 6.89 (s, 2H), 7.18–7.22 (m, 4H), 7.24–7.37 (m, 16H). MS (direct): 538 (M$^+$); 359, 73, 45.

Comparative Compound 1

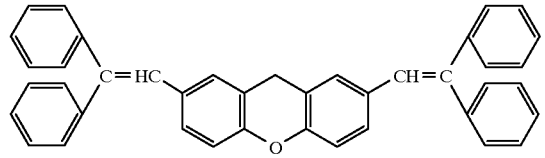

SYNTHESIS EXAMPLE 2

Synthesis of 4,4'-Bis(2'',2''-diphenylvinylphenyl)-methylamine (Comparative Compound 2)

Reaction was conducted using 3.0 g (12.5 mmol) of methyldi(p-formylphenyl)amine, 9.5 g (29.4 mmol) of diethyl diphenylmethylphosphonate (3a), 50 ml of DMF, and 3.4 g (30.3 mmol) of potassium t-butoxide in the same manner as in Example 1 (3). The resultant reaction mixture was treated in the same manner to obtain 5.05 g of Comparative Compound 2.

Yield, 74.9%; m.p., 169°–170° C.

Comparative Compound 2

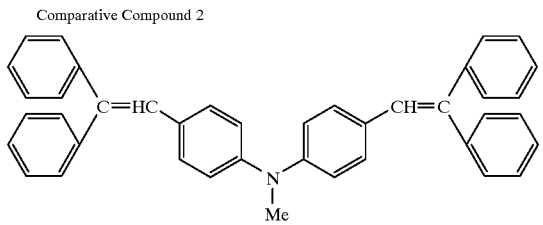

APPLICATION EXAMPLE 1

On a thin aluminum film formed on a polyester film by vapor deposition, oxotitanium phthalocyanine (TiOPc) was vacuum-deposited at $10^{-6}$ Torr in a thickness of about 0.8 μm to form a charge-generating layer. One part of Exemplified Compound 4 was mixed with 1 part of a polycarbonate resin represented by structural formula (H) (Polycarbonate Z-200, manufactured by Mitsubishi Gas Chemical Company, Inc.) in 8 parts of dichloroethane to dissolve the solid ingredients. This solution was applied on the charge-generating layer with a doctor blade and dried at 80° C. for 3 hours. Thus, a photoreceptor was produced. The electrophotographic photoreceptor thus obtained was statically examined for electrophotographic properties with electrostatic recording tester Type EPA-8200 (manufactured by Kawaguchi Electric Works, Japan) as follows. The photoreceptor was electrostatically charged by −6 kV corona discharge to measure the resultant surface potential $V_0$ (unit: −V). The charged photoreceptor was placed in the dark for 5 seconds (surface potential, Vi (unit: −V)), and then irradiated with light from a halogen lamp at an illuminance of 5 lux to determine the exposure required for the surface potential Vi to decrease by half, i.e., half-decay exposure $E_{1/2}$ (lux.sec), the exposure required for the surface potential to decrease to one sixth, $E_{1/6}$, and the residual surface potential $V_{R10}$ (−V) after 10-second irradiation at an illuminance of 5 lux. The results obtained are shown in Table 5.

APPLICATION EXAMPLES 2 AND 3

Photoreceptors were produced and evaluated for electrophotographic properties in the same manner as in Application Example 1, except that each of Exemplified Compounds 12 and 23 was used in place of Exemplified Compound 4. The results obtained are shown in Table 5.

COMPARATIVE EXAMPLE 1

A photoreceptor was produced and evaluated for electrophotographic properties in the same manner as in Application Example 1, except that Comparative Compound 1 was used in place of Exemplified Compound 4. The results obtained are shown in Table 5. Since this photoreceptor showed no photodecay, its $E_{1/2}$ and $E_{1/6}$ were unable to be determined.

COMPARATIVE EXAMPLE 2

A photoreceptor was produced and evaluated for electrophotographic properties in the same manner as in Application Example 1, except that Comparative Compound 2 was used in place of Exemplified Compound 4. The results obtained are shown in Table 5. The $E_{1/6}$ of this photoreceptor was unable to be determined.

Table 5 shows that the electrophotographic photoreceptors each employing a compound according to the present invention had better sensitivity and a lower residual potential than those employing Comparative Compounds.

APPLICATION EXAMPLE 4

One part of chlorodian blue (CDB) was kneaded together with 1 part of a polycarbonate resin (Yupilon E-2000, manufactured by Mitsubishi Gas Chemical Company, Inc.) in a ball mill for 5 hours using 30 parts of dichloroethane as a solvent. The pigment dispersion obtained was applied with a wire-wound bar on a sheet obtained by vapor-depositing aluminum on a poly(ethylene terephthalate) (PET) film, and the coating was dried at 45° C. for 3 hours to form a charge-generating layer having a thickness of about 1 μm. One part of Exemplified Compound 4 was mixed with 1 part of a polycarbonate resin represented by structural formula (H) (Polycarbonate Z, manufactured by Mitsubishi Gas Chemical Company, Inc.) in 8 parts of dichloroethane to dissolve the solid ingredients. This solution was applied on the charge-generating layer with a doctor blade and dried at 80° C. for 3 hours to produce a photoreceptor. The electrophotographic properties of the photoreceptor were evaluated in the same manner as in Application Example 1. The results obtained are shown in Table 6.

APPLICATION EXAMPLES 5 AND 6

Photoreceptors were produced and evaluated for electrophotographic properties in the same manner as in Application Example 4, except that each of Exemplified Compounds 12 and 23 was used in place of Exemplified Compound 4. The results obtained are shown in Table 6.

COMPARATIVE EXAMPLE 3

A photoreceptor was produced and evaluated for electrophotographic properties in the same manner as in Application Example 4, except that Comparative Compound 1 was used in place of Exemplified Compound 4. The results obtained are shown in Table 6. Since this photoreceptor showed no photodecay, its $E_{1/2}$ and $E_{1/6}$ were unable to be determined.

COMPARATIVE EXAMPLE 4

A photoreceptor was produced and evaluated for electrophotographic properties in the same manner as in Application Example 4, except that Comparative Compound 2 was used in place of Exemplified Compound 4. The results obtained are shown in Table 6. The $E_{1/6}$ of this photoreceptor was unable to be determined.

Table 6 shows that the electrophotographic photoreceptors each employing a compound according to the present invention had better sensitivity and a lower residual potential than those employing Comparative Compounds.

APPLICATION EXAMPLE 7

According to the method described in JP-A-1-291256, 40 parts of crystalline oxytitanium phthalocyanine was added to a binder resin solution obtained by dissolving 35 parts of a butyral resin poly(vinyl butyral) BL-1, manufactured by Sekisui Chemical Co., Ltd., Japan) in 1,425 parts of tetrahydrofuran, and the pigment was dispersed by treating the mixture with an oscillating mill for 2 hours together with glass beads. This dispersion was applied with a wire-wound bar on a sheet obtained by vapor-depositing aluminum on a poly(ethylene terephthalate) (PET) film, and the coating was dried to form a charge-generating layer.

One part of Exemplified Compound 12 was mixed with 1 part of a polycarbonate resin represented by structural formula (H) (Polycarbonate Z. manufactured by Mitsubishi Gas Chemical Company, Inc.) in 8 parts of dichloroethane to dissolve the solid ingredients. This solution was applied on the charge-generating layer with a doctor blade and dried at 80° C. for 3 hours to produce a photoreceptor. The electrophotographic properties of the photoreceptor thus obtained were examined in the same manner as in Application Example 1. The results obtained are shown in Table 7.

APPLICATION EXAMPLE 8

A photoreceptor was produced and evaluated for electrophotographic properties in the same manner as in Application Example 7, except that Exemplified Compound 23 was used in place of Exemplified Compound 12. The results obtained are shown in Table 7.

COMPARATIVE EXAMPLE 5

A photoreceptor was produced and evaluated for electrophotographic properties in the same manner as in Application Example 7, except that Comparative Compound 1 was used in place of Exemplified Compound 12. The results obtained are shown in Table 7. Since this photoreceptor showed no photodecay, its $E_{1/2}$ and $E_{1/6}$ were unable to be determined.

Table 7 shows that the electrophotographic photoreceptors each employing a compound according to the present invention had better sensitivity and a lower residual potential than that employing a Comparative Compound.

APPLICATION EXAMPLE 9

One part of τ-form metal-free phthalocyanine (τ-$H_2$Pc) was kneaded together with 1 part of a butyral resin poly (vinyl butyral) BL-1, manufactured by Sekisui Chemical Co., Ltd.) in a ball mill for 5 hours using 30 parts of tetrahydrofuran as a solvent. The pigment dispersion obtained was applied on a sheet obtained by vapor-depositing aluminum on a polyethylene terephthalate (PET) film, and the coating was dried at 50° C. for 2 hours. One part of Exemplified Compound 23 was mixed with 1 part of a polycarbonate resin represented by structural formula (H) (Polycarbonate Z, manufactured by Mitsubishi Gas Chemical Company, Inc.) in 8 parts of dichloroethane to dissolve the solid ingredients. This solution was applied on the charge-generating layer with a doctor blade and dried at 80° C. for 3 hours to produce a photoreceptor. The electrophotographic properties of this photoreceptor were evaluated in the same manner as in Application Example 1. The results obtained are shown in Table 8.

COMPARATIVE EXAMPLE 6

A photoreceptor was produced and evaluated for electrophotographic properties in the same manner as in Application Example 9, except that Comparative Compound 1 was used in place of Exemplified Compound 23. The results obtained are shown in Table 8. Since this photoreceptor showed no photodecay, its $E_{1/2}$ and $E_{1/6}$ were unable to be determined.

Table 8 shows that the electrophotographic photoreceptor employing a compound according to the present invention had better sensitivity and a lower residual potential than that employing a Comparative Compound.

APPLICATION EXAMPLE 10

One part by weight of x-form metal-free phthalocyanine (x-$H_2$Pc) was kneaded together with 1 part by weight of a butyral resin (Polyvinyl butyral BM-1, manufactured by Sekisui Chemical Co., Ltd.) in a ball mill for 5 hours using 30 parts by weight of tetrahydrofuran as a solvent. The pigment dispersion obtained was applied on a sheet obtained by vapor-depositing aluminum on a polyethylene terephthalate) (PET) film, and the coating was dried at 50° C. for 2 hours. One part by weight of Exemplified Compound 12 and 1 part by weight of a polycarbonate resin represented by structural formula (H) (Polycarbonate Z, manufactured by Mitsubishi Gas Chemical Company, Inc.) were dissolved in 8 parts by weight of dichloroethane. This solution was applied on the charge-generating layer with a doctor blade and dried at 80° C. for 2 hours to produce a photoreceptor. The electrophotographic properties of the photoreceptor thus obtained were examined in the same manner as in Application Example 1. The results obtained are shown in Table 9.

APPLICATION EXAMPLE 11

A charge-generating layer containing chlorodian blue was formed in the same manner as in Application Example 4. One part by weight of Exemplified Compound 4 and 1 part by weight of a bisphenol A/biphenol type copolycarbonate resin represented by structural formula (M) (manufactured by Idemitsu Kosan Co., Ltd., Japan) were dissolved in 8 parts by weight of dichloroethane. This solution was applied on the charge-generating layer with a doctor blade and dried at 80° C. for 2 hours to produce a photoreceptor. The electrophotographic properties of the photoreceptor thus obtained were examined in the same manner as in Application Example 1. The results obtained are shown in Table 10.

APPLICATION EXAMPLE 12

A charge-generating layer containing chlorodian blue was formed in the same manner as in Application Example 4. One part by weight of Exemplified Compound 12 and 1 part by weight of a bisphenol A/biphenol type copolycarbonate resin represented by structural formula (M) (manufactured by Idemitsu Kosan Co., Ltd.) were dissolved in 8 parts by weight of dichloroethane. This solution was applied on the charge-generating layer with a doctor blade and dried at 80° C. for 2 hours to produce a photoreceptor. The electrophotographic properties of the photoreceptor thus obtained were examined in the same manner as in Application Example 1. The results obtained are shown in Table 10.

COMPARATIVE EXAMPLE 7

A charge-generating layer containing chlorodian blue was formed in the same manner as in Application Example 4. One part by weight of Comparative Compound 2 and 1 part by weight of a bisphenol A/biphenol type copolycarbonate resin represented by structural formula (M) (manufactured by Idemitsu Kosan Co., Ltd.) were dissolved in 8 parts by weight of dichloroethane. This solution was applied on the charge-generating layer with a doctor blade and dried at 80° C. for 2 hours to produce a photoreceptor. The electrophotographic properties of the photoreceptor thus obtained were examined in the same manner as in Application Example 1. The results obtained are shown in Table 10. Since this photoreceptor had insufficient sensitivity, its $E_{1/6}$ was unable to be determined.

Table 10 shows that the electrophotographic photoreceptors each employing a compound according to the present invention had better sensitivity and a lower residual potential than that employing a Comparative Compound.

APPLICATION EXAMPLE 13

A charge-generating layer containing a crystalline oxytitanium phthalocyanine was formed in the same manner as in Application Example 7. One part by weight of Exemplified Compound 4 and 1 part by weight of a bisphenol A/biphenol type copolycarbonate resin represented by structural formula (M) (manufactured by Idemitsu Kosan Co., Ltd.) were dissolved in 8 parts by weight of dichloroethane. This solution was applied on the charge-generating layer with a doctor blade and dried at 80° C. for 2 hours to produce a photoreceptor. The electrophotographic properties of the photoreceptor thus obtained were examined in the same manner as in Application Example 1. The results obtained are shown in Table 11.

APPLICATION EXAMPLE 14

A charge-generating layer containing a crystalline oxytitanium phthalocyanine was formed in the same manner as in Application Example 7. One part by weight of Exemplified Compound 12 and 1 part by weight of a bisphenol A/biphenol type copolycarbonate resin represented by structural formula (M) (manufactured by Idemitsu Kosan Co., Ltd.) were dissolved in 8 parts by weight of dichloroethane. This solution was applied on the charge-generating layer with a doctor blade and dried at 80° C. for 2 hours to produce a photoreceptor. The electrophotographic properties of the photoreceptor thus obtained were examined in the same manner as in Application Example 1. The results obtained are shown in Table 11.

COMPARATIVE EXAMPLE 8

A charge-generating layer containing a crystalline oxytitanium phthalocyanine was formed in the same manner as in Application Example 7. One part by weight of Comparative Compound 2 and 1 part by weight of a bisphenol A/biphenol type copolycarbonate resin represented by structural formula (M) (manufactured by Idemitsu Kosan Co., Ltd.) were dissolved in 8 parts by weight of dichloroethane. This solution was applied on the charge-generating layer with a doctor blade and dried at 80° C. for 2 hours to produce a photoreceptor. The electrophotographic properties of the photoreceptor thus obtained were examined in the same manner as in Application Example 1. The results obtained are shown in Table 11. Since this photoreceptor had insufficient sensitivity, its $E_{1/6}$ was unable to be determined.

Table 11 shows that the electrophotographic photoreceptors each employing a compound according to the present invention had better sensitivity and a lower residual potential than that employing a Comparative Compound.

TABLE 5

|  | Charge-transporting material | Charge-generating material | Polymeric binder | $V_0$ (-V) | $V_i$ (-V) | $V_{R10}$ (-V) | $E_{1/2}$ (lux · sec) | $E_{1/6}$ (lux · sec) |
|---|---|---|---|---|---|---|---|---|
| Application Example 1 | Exemplified Compound 4 | vapor-deposited TiOPc | H | 1159 | 924 | 0 | 0.75 | 1.79 |
| Application Example 2 | Exemplified Compound 12 | vapor-deposited TiOPc | H | 973 | 712 | 35 | 0.83 | 1.98 |
| Application Example 3 | Exemplified Compound 23 | vapor-deposited TiOPc | H | 1022 | 827 | 1 | 1.20 | 2.47 |
| Comparative Example 1 | Comparative Compound 1 | vapor-deposited TiOPc | H | 1098 | 944 | 488 | unable to be measured | unable to be measured |
| Comparative Example 2 | Comparative Compound 2 | vapor-deposited TiOPc | H | 1212 | 1040 | 248 | 5.22 | unable to be measured |

TABLE 6

|  | Charge-transporting material | Charge-generating material | Polymeric binder | $V_0$ (-V) | $V_i$ (-V) | $V_{R10}$ (-V) | $E_{1/2}$ (lux · sec) | $E_{1/6}$ (lux · sec) |
|---|---|---|---|---|---|---|---|---|
| Application Example 4 | Exemplified Compound 4 | CDB | H | 878 | 725 | 0 | 3.91 | 8.80 |
| Application Example 5 | Exemplified Compound 12 | CDB | H | 772 | 596 | 55 | 3.13 | 8.39 |
| Application Example 6 | Exemplified Compound 23 | CDB | H | 585 | 301 | 1 | 1.66 | 3.52 |
| Comparative Example 3 | Comparative Compound 1 | CDB | H | 1167 | 1123 | 911 | unable to be measured | unable to be measured |
| Comparative Example 4 | Comparative Compound 2 | CDB | H | 1356 | 1235 | 468 | 22.96 | unable to be measured |

TABLE 7

| | Charge-transporting material | Charge-generating material | Polymeric binder | $V_0$ (-V) | Vi (-V) | $V_{R10}$ (-V) | $E_{1/2}$ (lux · sec) | $E_{1/6}$ (lux · sec) |
|---|---|---|---|---|---|---|---|---|
| Application Example 7 | Exemplified Compound 12 | crystalline TiOPc | H | 807 | 525 | 0 | 0.45 | 1.08 |
| Application Example 8 | Exemplified Compound 23 | crystalline TiOPc | H | 1022 | 827 | 1 | 1.20 | 2.47 |
| Comparative Example 5 | Comparative Compound 1 | crystalline TiOPc | H | 1140 | 1056 | 1016 | unable to be measured | unable to be measured |

TABLE 8

| | Charge-transporting material | Charge-generating material | Polymeric binder | $V_0$ (-V) | Vi (-V) | $V_{R10}$ (-V) | $E_{1/2}$ (lux · sec) | $E_{1/6}$ (lux · sec) |
|---|---|---|---|---|---|---|---|---|
| Application Example 9 | Exemplified Compound 23 | $\tau$-$H_2$Pc | H | 707 | 376 | 61 | 0.89 | 22.91 |
| Comparative Example 6 | Comparative Compound 1 | $\tau$-$H_2$Pc | H | 694 | 499 | 426 | unable to be measured | unable to be measured |

TABLE 9

| | Charge-transporting material | Charge-generating material | Polymeric binder | $V_0$ (-V) | Vi (-V) | $V_{R10}$ (-V) | $E_{1/2}$ (lux · sec) | $E_{1/6}$ (lux · sec) |
|---|---|---|---|---|---|---|---|---|
| Application Example 10 | Exemplified Compound 12 | $x$-$H_2$Pc | H | 815 | 561 | 8 | 2.16 | 4.77 |

TABLE 10

| | Charge-transporting material | Charge-generating material | Polymeric binder | $V_0$ (-V) | Vi (-V) | $V_{R10}$ (-V) | $E_{1/2}$ (lux · sec) | $E_{1/6}$ (lux · sec) |
|---|---|---|---|---|---|---|---|---|
| Application Example 11 | Exemplified Compound 4 | CDB | M | 712 | 510 | 0 | 3.17 | 7.23 |
| Application Example 12 | Exemplified Compound 12 | CDB | M | 712 | 573 | 1 | 2.93 | 6.48 |
| Comparative Example 7 | Comparative Compound 2 | CDB | M | 993 | 848 | 186 | 12.57 | unable to be measured |

TABLE 11

| | Charge-transporting material | Charge-generating material | Polymeric binder | $V_0$ (-V) | Vi (-V) | $V_{R10}$ (-V) | $E_{1/2}$ (lux · sec) | $E_{1/6}$ (lux · sec) |
|---|---|---|---|---|---|---|---|---|
| Application Example 13 | Exemplified Compound 4 | crystalline TiOPc | M | 804 | 498 | 6 | 0.51 | 1.38 |
| Application Example 14 | Exemplified Compound 12 | crystalline TiOPc | M | 512 | 369 | 31 | 0.51 | 2.93 |
| Comparative Example 8 | Comparative Compound 2 | crystalline TiOPc | M | 727 | 380 | 146 | 23.38 | unable to be measured |

The charge-transporting material obtained according to the present invention has good solubility in binder polymers. The electrophotographic photoreceptor employing the charge-transporting material has excellent electrophotographic properties including satisfactory sensitivity and a low residual potential, and is hence extremely useful.

While the invention has been described in detail and with reference to specific embodiments thereof, it will be apparent to one skilled in the art that various changes and modifications can be made therein without departing from the spirit and scope thereof.

What is claimed is:

1. A phenothiazine or phenoxazine derivative represented by the following formula (1):

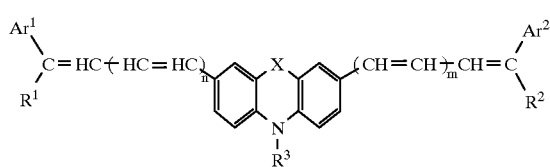

wherein $Ar^1$ and $Ar^2$ may be the same or different and each represents an aryl group which may have one or more substituents selected from the group consisting of a lower alkyl group, a lower alkoxy group, a halogen atom, a diarylamino group, and a dialkylamino group; $R^1$ and $R^2$ may be the same or different and each represents a hydrogen atom, a lower alkyl group, or an aryl group which may have one or more substituents selected from the group consisting of a lower alkyl group, a lower alkoxy group, a halogen atom, a diarylamino group, and a dialkylamino group; $R^3$ represents a lower alkyl group, an alicyclic hydrocarbon group having 5 to 7 carbon atoms, an aryl group which may have one or more substituents selected from the group consisting of a lower alkyl group, a lower alkoxy group, a halogen atom, a diarylamino group, and a dialkylamino group, or an aralkyl group which may have one or more substituents selected from the group consisting of a benzyl group, a tolylmethyl group, a methoxybenzyl group, and a chlorobenzyl group; X represents a sulfur atom or an oxygen atom; and n and m each represents an integer of 0 or 1.

* * * * *